(12) United States Patent
Strom et al.

(10) Patent No.: US 8,809,280 B2
(45) Date of Patent: Aug. 19, 2014

(54) THERAPEUTIC PEPTIDES

(75) Inventors: Morten Strom, Tromso (NO); Terkel Hansen, Tromso (NO); Martina Havelkova, Tromso (NO); Veronika Torfoss, Krokelvdalen (NO)

(73) Assignee: Lytix Biopharma AS, Tromso (NO)

( * ) Notice: Subject to any disclaimer, the term of this patent is extended or adjusted under 35 U.S.C. 154(b) by 0 days.

(21) Appl. No.: 13/505,625

(22) PCT Filed: Nov. 2, 2010

(86) PCT No.: PCT/GB2010/002024
§ 371 (c)(1),
(2), (4) Date: Oct. 22, 2012

(87) PCT Pub. No.: WO2011/051692
PCT Pub. Date: May 5, 2011

(65) Prior Publication Data
US 2013/0035296 A1    Feb. 7, 2013

(30) Foreign Application Priority Data

Nov. 2, 2009 (GB) .................................. 0919194.1

(51) Int. Cl.

| | | |
|---|---|---|
| *A01N 37/18* | (2006.01) |
| *A61K 38/00* | (2006.01) |
| *A61P 31/04* | (2006.01) |
| *A61P 35/00* | (2006.01) |
| *A61K 38/06* | (2006.01) |
| *A61K 38/07* | (2006.01) |
| *A61K 31/4965* | (2006.01) |
| *A61K 31/165* | (2006.01) |
| *A61K 31/16* | (2006.01) |
| *C07C 233/00* | (2006.01) |
| *C07C 235/00* | (2006.01) |
| *C07C 237/00* | (2006.01) |
| *C07C 239/00* | (2006.01) |
| *A61K 38/04* | (2006.01) |
| *C07K 5/00* | (2006.01) |
| *C07K 7/00* | (2006.01) |
| *C07K 16/00* | (2006.01) |
| *C07K 17/00* | (2006.01) |
| *C07D 295/00* | (2006.01) |

(52) U.S. Cl.
USPC .......... 514/21.9; 514/2.4; 514/19.2; 514/620; 514/623; 514/626; 514/255.01; 530/330; 564/164; 564/188; 564/197; 544/391

(58) Field of Classification Search
CPC ..................................................... A61K 38/00
See application file for complete search history.

(56) References Cited

U.S. PATENT DOCUMENTS

| | | | |
|---|---|---|---|
| 4,342,705 A | 8/1982 | Maender et al. |
| 4,894,384 A | 1/1990 | Cecere et al. |
| 5,134,123 A | 7/1992 | Branca et al. |
| 5,593,967 A | 1/1997 | Horwell et al. |
| 5,976,758 A | 11/1999 | Fukui et al. |
| 6,080,767 A | 6/2000 | Klein et al. |
| 6,323,227 B1 | 11/2001 | Klein et al. |

FOREIGN PATENT DOCUMENTS

| | | | |
|---|---|---|---|
| DE | 102006018080 A1 | | 10/2007 |
| DE | 102006018080 A1 | * | 10/2007 |
| EP | 0123931 A2 | | 11/1984 |
| EP | 310918 A2 | | 4/1989 |
| EP | 2105433 A1 | * | 9/2009 |
| EP | 2105433 A1 | | 9/2009 |
| WO | 92/04045 A1 | | 3/1992 |
| WO | WO-9212168 A1 | | 7/1992 |
| WO | 97/24118 A1 | | 7/1997 |
| WO | 98/57174 A1 | | 12/1998 |

OTHER PUBLICATIONS

Eliopoulous GM "Antimicrobial agents for treatment of serious infections caused by resistant *Staphylococcus aureus* and *enterococci*" Eur J Clin Microbiol Infect Dis 24:826-831. Published online Nov. 29, 2005.*
Page M and Heim J "Prospects for the next anti-*Pseudomonas* drug" Curr Opin in Pharmacol 9:558-565. Published online Sep. 12, 2009.*
Verma et al "Defensins: antimicrobial peptides for therapeutic development" Biotechnol J 2:1353-1359. Published online Sep. 20, 2007.*
Stroem et al: "The pharmacophore of short cationic antibacterial peptides", Journal of Medicinal Chemistry 46(9): 1567-1570. (2003).

(Continued)

*Primary Examiner* — Maury Audet
*Assistant Examiner* — Zachary J Miknis
(74) *Attorney, Agent, or Firm* — Fox Rothschild LLP

(57) ABSTRACT

The present invention provides a peptide, peptidomimetic or amino acid derivative having a net positive charge of at least +2 and incorporating a disubstituted β amino acid, each of the substituting groups in the β amino acid, which may be the same or different, comprises at least (7) non-hydrogen atoms, is lipophilic and has at least one cyclic group, one or more cyclic groups within a substituting group may be linked or fused to one or more cyclic groups within the other substituting group and where cyclic groups are fused in this way the combined total number of non-hydrogen atoms for the two substituting groups is at least (12), for use as a cytolytic therapeutic agent; as well as non therapeutic uses of these molecules and certain defined novel compounds from within this definition.

37 Claims, 4 Drawing Sheets

(56) References Cited

OTHER PUBLICATIONS

Hansen et al: "Antimicrobial activity of small beta-peptidomimetics based on the pharmacophore model of short cationic antimicrobial peptides." Journal of Medicinal Chemistry 53(2): 595-606. (2010).
Abele, et al, "Preparation of Achiral and of Enantiopure Geminally Disubstituted beta-Amino Acids for beta-Peptide Synthesis" Eur. J. Org. Chem. 2000 (2000), 1-15.
Cronin, et al, "Gas chromatographic-mass spectral analysis of the five-carbon beta-, gamma-, and delta-amino alkanoic acids" Anal. Biochem. 124 (1982), 139-49.
Seebach, et al, "Preparation and Structure of beta-Peptides Consisting of Geminally Disubstituted beta2,2- and beta3,3-Amino Acids: A Turn Motif for beta-Peptides" Helv. Chim. Acta 81 (1998), 2218-43.
Molinero, et al, "Synthesis and properties of lipopeptidic surfactants" Peptides (1990), 436-7.
Renau, et al, "Inhibitors of Efflux Pumps in *Pseudomonas aeruginosa* Potentiate the Activity of the Fluoroquinolone Antibacterial Levofloxacin" J. Med. Chem. 42 (1999), 4928-31.
Nedev, et al, "Synthesis of L-lysine containing peptides with antibacterial activity" Doklady Bolgarskoi Akademi Nauk 42 (1989), 31-4.
Heinonen, et al "Synthesis of Achiral , beta-disubstituted beta-alanines, and their use in construction of libraries of beta-peptide conjugates of N-2-alkyl-1,2,3,4-tetrahydroisoquinolines on a solid support" Tetrahedron 55 (1999), 7613-24.
Zhang, et al "Binding of matrix metalloproteinase inhibitors to extracellular matrix: 3D-QSAR analysis" Chem. Biol. & Drug Des. 72 (2008), 237-48.
Sibi, et al "The Role of Achiral Pyrazolidinone Templates in Enantioselective Diels-Alder Reactions: Scope, Limitations, and Conformational Insights" JACS 129 (2007), 395-405.
Sibi, et al "Exo Selective Enantioselective Nitrone Cycloadditions" JACS 126 (2004), 718-9.
Berger, et al "Antiprotozoal activities of new bis-chlorophenyl derivatives of bicyclic octanes and aza-nonanes" Bioorg. Med. Chem. Let. 16 (2006), 5457-61.
Seebacher, Werner, et al "Synthesis of 2-azabicyclo[3.2.2]nonanes from bicyclo[2.2.2]octan-2-ones and their activities against *Trypanosoma brucei* rhodesiense and *Plasmodium falciparum* K1" J. Pharm. Pharm. Sci. 8 (2005), 578-85.
Taubinger, et al "Synthesis of beta, beta'-diamino acids from alpha-amino acid derived beta-lactams by ring opening with nucleophiles. Utilization in the synthesis of peptidomimetics" Tetrahedron 64 (2008), 8659-67.
Taubinger, et al "Synthesis of beta, beta'-diamino acids from alpha-amino acid derived beta-lactams" Synlett (2008), 539-42.
Capone, Stefania, et al "Highly diastereoselective preparation of anti-alpha, beta-dialkyl beta-amino acids containing natural alpha-amino acid side chains" Tetrahedron, 63 (2007), 12202-6.
Ciez, Dariusz "Titanium(IV)-mediated synthesis of 2,3-diisothiocyanato-succinic acid diesters and 3,6-dithioxo-piperazine derivatives" Tetrahedron, 63 (2007), 4510-5.
Taha, Mutasem O., et al "Ligand-based assessment of factor Xa binding site flexibility via elaborate pharmacophore exploration and genetic algorithm-based QSAR modeling" Eur. J. Med. Chem., 40 (2005), 701-27.
Czekaj, Mark, et al "Optimization of the beta-Aminoester class of factor Xa inhibitors. part 1: P4 and side-Chain modifications for improved in vitro potency" Bioorg. Med. Chem. Let., 12 (2002), 1667-70.
Reginato, Gianna, et al "Synthesis of non-racemic beta-branched alpha-(aminoalkyl)-acrylates from naturally occurring amino acids" Tetrahedron: Asymmetry, 13 (2002), 595-600.
Seki, Masahiko, et al "Stereoselective synthesis of beta-benzyl-alpha alkyl-beta-amino acids from L-aspartic acid" J. Org. Chem., 65 (2000), 1298-304.
Wang, Jianbo, et al "Stereoselective synthesis of enantiomerically pure 4,5-disubstituted pyrrolidinones from beta-amino esters" Tetrahedron: Asymmetry, 10 (1999), 4553-61.
Ettmayer, Peter, et al "Addition of dilithiated methyl-3-aminobutanoate to aldehydes proceeds with ul-1,2-induction" Tetrahedron Let., 35 (1994), 3901-4.
Chandler, Carley, et al "The proline-catalysed double Mannich reaction of acetaldehyde with N-boc imines" Angew. Chem. Int. Ed., 48 (2009), 1978-90.
Stamm, Helmut & Steudle, Harald "Nitrones, part 8. Isoxazolidine compounds, part 7. Reformatskii reaction with ketonitrones, Slow N-inversion in the 5-isoxazolidinone ring" Archie der Pharmazie, 310 (1977), 873-81.

* cited by examiner

THERAPEUTIC PEPTIDES

The present application is the U.S. National Phase of International Patnet Application Serial No. PCT/GB2010/002024, filed Nov. 2, 2010, which claims priority to U.K. Patent Application Serial No. 0919194.1, filed Nov. 2, 2009. The foregoing applications are hereby incorporated by reference in their entireties.

The present invention relates to modified amino acids, peptides and peptidomimetics and their use as cytolytic agents, these cytolytic agents find particular utility as antimicrobial and antitumoural agents.

Infections caused by multi-resistant bacteria have become a major concern to society over the past 20-25 years. This is especially a problem in hospitals where infections caused by methicillin resistant *Staphylococcus aureus* (MRSA), vancomycin resistant *Staphylococcus aureus* (VRSA) and methicillin resistant *Staphylococcus epidermidis* (MRSE) can result in severe injury, prolonged hospitalisation and death, especially among immune compromised patients. Vancomycin was once a drug of last resort, but reports from hospitals around the world show that infrequent use of vancomycin is no longer the case.

As well as the above Gram-positive species, clinicians are also reporting problems with multiresistant Gram-negative species including *Pseudomonas aeruginosa* and *Eschericha coli*. It would be highly desirable if a single antibiotic molecule exhibited activity against a broad spectrum of bacteria, including both Gram-positive and Gram-negative species.

There has been a draught among the largest pharmaceutical companies for developing novel classes of antimicrobial compounds, apparently due to huge costs of development and relatively limited duration of patient treatment as compared to treatment of chronic diseases. However, the need for novel antimicrobial agents is urgent and in the US deaths caused by hospital acquired infections are currently superseding HIV-related mortality.

A promising class of antimicrobial agents are cationic antimicrobial peptides (AMP's), also known as host defence peptides. AMP's have a unique mode of action by targeting the inner and/or outer membranes of bacteria in a non-receptor specific manner. The detailed mechanism of membrane disruption by AMP's is still not fully understood, and various models have been proposed to explain the observed effects.

Due to the relative similarity between the lipid cell membrane components of prokaryotes and eukaryotic tumour cells, a selective membrane destabilising and eventually lytic activity against tumour cells has also been observed for these antimicrobial peptides. For both target cell types an effective class of amphipathic peptides and peptide-like molecules has been identified which have a net positive charge and a lipophilic group or groups. While for the first generation of these molecules a pore-forming mode of action was assumed and they typically incorporated ten or more amino acids, it has more recently been shown that much smaller molecules can retain therapeutically relevant levels of activity and selectivity (Strøm M. B. et al., J. Med. Chem. 2003, 46, 1567-1570).

Nevertheless, the sometimes conflicting objectives of therapeutic activity, selectivity, toxicity, in vivo and in vitro stability, cost of production and ease of delivery means there is a constant need to develop new drug candidates within this general class of molecule.

The present inventors have found that by utilising a disubstituted β amino acid a new class of cytolytic molecule can be generated which has highly promising activity and other desirable characteristics, including a broad spectrum of antibacterial activity, for example activity against both Gram-positive and Gram-negative species. Preferably the molecules are suitable for oral delivery.

Thus, in one aspect, the present invention provides a peptide, peptidomimetic or (modified) amino acid having a net positive charge of at least +2 and incorporating a disubstituted β amino acid, each of the substituting groups in the β amino acid, which may be the same or different, comprises at least 7 non-hydrogen atoms, is lipophilic and has at least one cyclic group, one or more cyclic groups within a substituting group may be linked or fused to one or more cyclic groups within the other substituting group and where cyclic groups are fused in this way the combined total number of non-hydrogen atoms for the two substituting groups is at least 12, for use as a cytolytic therapeutic agent. The 2 substituting groups on the β amino acid are preferably the same.

Without wishing to be bound by theory, it seems the inclusion of a disubstituted β amino acid increases stability of the molecule, and though the forced conformational charges improves the amphipathicity of the molecule, as well as causing a powerful disruptive effect on the membrane due to the repulsive interactions of the two lipophilic moieties in the disubstituted residue. This gives a cytolytic effect which can be cytotoxic.

The cytolytic activity may be an antimicrobial, preferably an antibacterial activity and/or an antitumoural activity and such medical uses constitute preferred embodiments of the present invention. Thus the present invention provides the peptides, peptidomimetics and modified amino acids as defined above (and described in more detail below) for use as cytolytic antimicrobial or antitumoural agents. Alternatively viewed, the present invention provides the peptides, peptidomimetics and modified amino acids as defined above (and described in more detail below) for use in treating a microbial (particularly a bacterial) infection or for treating tumour cells (particularly a solid tumour).

Microbes which may be targeted or treated include, bacteria (Gram positive and Gram negative), fungi, archaea and protists. Bacteria are of particular interest due to their ability to infect humans and other animals in health and life-threatening ways.

Preferred bacterial targets include Gram positive bacteria, in particular *Staphylococcus aureus*, methicillin resistant *Staphylococcus aureus* (MRSA) and methicillin resistant *Staphylococcus epidermidis* (MRSE). Gram negative species such as *Pseudomonas aeruginosa* and *Eschericha coli* may also be treated. Chronic wounds are often infected by both Gram positive and Gram negative species and the treatment of a patient which has or is suspected of having or developing a multipathogen infection (e.g. at the site of a chronic wound) is a preferred use according to the present invention.

Antimicrobial activity also provides non-therapeutic uses e.g. as a disinfectant, and in a further aspect the present invention provides the ex vivo use of a peptide, peptidomimetic or modified amino acid as defined and described herein as a cytolytic agent.

Lipophilicity can be measured by a molecule's distribution in a biphasic system, e.g. liquid-liquid such as 1-octanol/water. It is well known in the art that polar substituents such as hydroxy, carboxy, carbonyl, amino and ethers decrease the partition coefficient in a biphasic system such as 1-octanol/water as they reduce lipophilicity; the lipophilic substituting groups will therefore preferably contain no more than two, more preferably one or no such polar groups.

A β amino acid has the amino group attached to the β carbon atom; genetically coded amino acids are a amino acids in which the amino group is attached to the α carbon atom.

This arrangement lengthens by one atom per β amino acid the backbone of a peptide incorporating one or more β amino acids. In this arrangement the α and/or the β carbon atom can be substituted. The α or β carbon atom may be disubstituted; where the α carbon atom is disubstituted a $β^{2,2}$ amino acid results and where the β carbon atom is disubstituted a $β^{3,3}$ amino acid is generated. One substituting group on each of the α or β carbon atoms results in a $β^{2,3}$ amino acid. $β^{2,2}$ and $β^{3,3}$ disubstituted amino acids are preferred for use in accordance with the invention, $β^{2,2}$ disubstituted amino acids being especially preferred.

The β amino acid is substituted by two groups incorporating at least 7 non-hydrogen atoms. Preferably one, more preferably both of the substituting groups contains at least 8, more preferably at least 10 non-hydrogen atoms. These groups are lipophilic in nature and while they may be different, are preferably the same. Each contains at least one cyclic group, typically a 6 membered ring which may be aliphatic or aromatic, preferably aromatic, and may be substituted, substituting groups may include hetero atoms such as oxygen, nitrogen, sulphur or a halogen, in particular fluorine or chlorine. Preferred substituting groups include $C_1$-$C_4$ alkyl (especially t-butyl), methoxy, fluoro and fluoromethyl groups. The cyclic groups may be homo- or heterocyclic, preferably they are homocyclic ring of carbon atoms. Preferred lipophilic substituting groups incorporate two or three cyclic groups, preferably two cyclic groups, which may be connected or fused, preferably fused. Particularly preferred substituting groups comprise a naphthalene group.

A further preferred group of lipophilic substituting groups have a single substituted or unsubstituted cyclic group, preferably a phenyl or cyclohexyl group.

The cyclic group or groups is typically spaced away from the peptide backbone (i.e. from the α or β carbon atom of the β amino acid) by a chain of 1 to 4, preferably 1 to 3 atoms; these linking atoms may include nitrogen and/or oxygen but will typically be carbon atoms, preferably the linking atoms are unsubstituted. These spacers are of course part of the substituting groups as defined herein.

Each substituting moiety of the disubstituted β amino acid will typically comprise 7 to 20 non-hydrogen atoms, preferably 7 to 13, more preferably 8 to 12, most preferably 9-11 non-hydrogen atoms.

The molecules for use according to the invention will preferably be peptides or peptidomimetics of 1 or 2 to 12 amino acids or equivalent subunits in length. Unless otherwise clear from the context, reference herein to 'amino acids' includes the equivalent subunit in a peptidomimetic. For antimicrobial purposes the preferred molecules have 1 to 3 or 4 amino acids, for antitumour purposes the preferred molecules are longer, e.g. 3 to 12 amino acids, more preferably 5 to 12 amino acids in length. As demonstrated in the Examples, molecules of use according to the invention may only comprise a single amino acid but this will be a 'modified' amino acid in order to fulfil the requirements for charge.

Single amino acids as well as peptides and peptidomimetics will preferably incorporate a modified C terminus, the C terminal modifying group typically resulting in charge reversal, i.e. removing the negative charge of the carboxyl group and adding a positive charge, e.g. through the presence of an amino group. This modification alone, assuming the N terminus is not modified, will give the molecule overall a net charge of +2. Whether the C terminus is modified to give charge reversal or simply to remove the negative charge of the carboxyl group, the molecule preferably also contains one or more cationic amino acids. Thus the overall charge of the molecule may be +3, +4 or higher for larger molecules.

Suitable C-terminal groups, which are preferably cationic in nature, will typically have a maximum size of 15 non-hydrogen atoms. The C-terminus is preferably amidated and the amide group may be further substituted to form an N-alkyl or N,N-dialkyl amide. Primary and secondary amide groups are preferred. Suitable groups to substitute the amide group include aminoalkyl, e.g. amino ethyl or dimethylaminoethyl; the nitrogen atom of the amide group may form part of a cyclic group e.g. pyrazolidine, piperidine, imidazolidine and piperazine, piperazine being preferred, these cyclic groups may themselves be substituted, for example by alkyl or aminoalkyl groups.

Peptides for use according to the invention preferably incorporate one or more cationic amino acids, lysine, arginine, ornithine and histidine are preferred but any non-genetically coded or modified amino acid carrying a positive charge at pH 7.0 may be incorporated.

Suitable non-genetically coded cationic amino acids and modified cationic amino acids include analogues of lysine, arginine and histidine such as homolysine, ornithine, diaminobutyric acid, diaminopimelic acid, diaminopropionic acid and homoarginine as well as trimethylysine and trimethylornithine, 4-aminopiperidine-4-carboxylic acid, 4-amino-1-carbamimidoylpiperidine-4-carboxylic acid and 4-guanidinophenylalanine.

Dipeptides will typically incorporate one cationic amino acid and longer peptides will usually incorporate additional cationic amino acids, thus a peptide of 4 or 5 amino acids may have 2 or 3 cationic amino acids and peptides of 6 to 9 amino acids may have 3 to 6 cationic amino acids.

A preferred group of molecules comprise a $β^{2,2}$ disubstituted amino acid coupled to a C-terminal L-arginine amide residue and dipeptides having this arrangement are particularly preferred.

Peptides with three or more amino acids will typically have one or more additional lipophilic amino acids, i.e. amino acids with a lipophilic R group. Typically the lipophilic R group has at least one, preferably two cyclic groups, which may be fused or connected. The lipophilic R group may contain hetero atoms such as O, N or S but typically there is no more than one heteroatom, preferably it is nitrogen. This R group will preferably have no more than 2 polar groups, more preferably none or one, most preferably none.

Tryptophan is a preferred lipophilic amino acid and peptides preferably comprise 1 to 3 tryptophan residues. Further genetically coded lipophilic amino acids which may be incorporated are phenylalanine and tyrosine.

The lipophilic amino acids may be non-genetically coded, including genetically coded amino acids with modified R groups.

A peptidomimetic is typically characterised by retaining the polarity, three dimensional size and functionality (bioactivity) of its peptide equivalent but wherein the peptide bonds have been replaced, often by more stable linkages. By 'stable' is meant more resistant to enzymatic degradation by hydrolytic enzymes. Generally, the bond which replaces the amide bond (amide bond surrogate) conserves many of the properties of the amide bond, e.g. conformation, steric bulk, electrostatic character, possibility for hydrogen bonding etc. Chapter 14 of "Drug Design and Development", Krogsgaard, Larsen, Liljefors and Madsen (Eds) 1996, Horwood Acad. Pub provides a general discussion of techniques for the design and synthesis of peptidomimetics. In the present case, where the molecule is reacting with a membrane rather than the specific active site of an enzyme, some of the problems described of exactly mimicking affinity and efficacy or substrate function are not relevant and a peptidomimetic can be readily prepared based on a given peptide structure or a motif of required functional groups. Suitable amide bond surrogates include the following groups: N-alkylation (Schmidt, R. et al., Int. J. Peptide Protein Res., 1995, 46, 47), retro-inverse amide (Chorev, M. and Goodman, M., Acc. Chem. Res, 1993, 26, 266), thioamide (Sherman D. B. and Spatola, A. F. J. Am. Chem. Soc., 1990, 112, 433), thioester, phosphonate, ketomethylene (Hoffman, R. V. and Kim, H. O. J. Org. Chem., 1995, 60, 5107), hydroxymethylene, fluorovinyl (Allmendinger, T. et al., Tetrahydron Lett., 1990, 31, 7297), vinyl, methyleneamino (Sasaki, Y and Abe, J. Chem. Pharm. Bull. 1997 45, 13), methylenethio (Spatola, A. F., Methods Neurosci, 1993, 13, 19), alkane (Lavielle, S. et. al., Int. J. Peptide Protein Res., 1993, 42, 270) and sulfonamido (Luisi, G. et al. Tetrahedron Lett. 1993, 34, 2391).

The molecules of the present invention contain a disubstituted β amino acid and various molecules are described in the Examples which contain only one further amino acid, i.e. molecules having 2 amino acids joined by an amide bond. Such molecules could be considered dipeptides because of the amide bond; however the amide bonds in these molecules are in fact non-scissile due to the disubstitution of the β amino acid and as such these molecules could be considered peptidomimetics. For the purposes of the present invention, such molecules (and larger molecules with more amino acids) are considered to be peptides (rather than peptidomimetics), due to the presence of an amide bond. This allows for clarity of nomenclature without requiring testing of whether, or to what extent, a given amide bond is scissile. In other words, if all the amino acids in a molecule are linked by amide bonds, the molecule is considered a peptide, even if one or more of the amide bonds is not readily scissile.

The peptidomimetic compounds of the present invention will typically have identifiable sub-units which are approximately equivalent in size and function to amino acids. Peptidomimetics will generally have groups equivalent to the R groups of amino acids and discussion herein of suitable R groups and of N and C terminal modifying groups applies, mutatis mutandis, to peptidomimetic compounds.

As is discussed in the text book referenced above, as well as replacement of amide bonds, peptidomimetics may involve the replacement of larger structural moieties with di- or tripeptidomimetic structures and in this case, mimetic moieties involving the peptide bond, such as azole-derived mimetics may be used as dipeptide replacements. Peptidomimetics and thus peptidomimetic backbones wherein just the amide bonds have been replaced as discussed above are, however, preferred.

Suitable peptidomimetics include reduced peptides where the amide bond has been reduced to a methylene amine by treatment with a reducing agent e.g. borane or a hydride reagent such as lithium aluminium-hydride. Such a reduction has the added advantage of increasing the overall cationicity of the molecule.

Other peptidomimetics include peptoids formed, for example, by the stepwise synthesis of amide-functionalised polyglycines. Some peptidomimetic backbones will be readily available from their peptide precursors, such as peptides which have been permethylated, suitable methods are described by Ostresh, J. M. et al. in Proc. Natl. Acad. Sci. USA (1994) 91, 11138-11142. Strongly basic conditions will favour N-methylation over O-methylation and result in methylation of some or all of the nitrogen atoms in the peptide bonds and the N-terminal nitrogen.

Preferred peptide bond replacements include esters, polyamines and derivatives thereof as well as substituted alkanes and alkenes, particularly aminomethyl and ketomethylene. The peptidomimetics will preferably have N and C termini which may be modified as discussed herein.

In a further aspect the present invention provides a method of treating or preventing a microbial infection, preferably a bacterial infection, which method comprises administration to a subject of a peptide, peptidomimetic or modified amino acid as defined above.

In a further aspect the present invention provides a method of treating tumour cells or preventing or reducing the growth, establishment spread, or metastasis of a tumour, which method comprises administration to a subject of a peptide, peptidomimetic or modified amino acid as defined above.

As used herein, treatment of a microbial/bacterial infection will preferably mean a reduction in the number of viable microbes/bacterial cells but may also include a bacteriostatic type activity where cell numbers are contained at numbers which are less harmful to the subject than if the infection had been allowed to proceed unchecked. 'Prevention' includes inhibition of microbial/bacterial cell growth such that a measurable and/or harmful population is not established in the treated subject.

Treated tumour cells may be circulating but will typically be part of a solid tumour; as with microbial cells, treatment will preferably involve cell death through cell lysis. Cell lysis may result in presentation of tumour cell antigens and the generation of an acquired immunity which can prevent or inhibit the development of secondary tumours.

In a further aspect the present invention provides a product comprising (a) a peptide, peptidomimetic or modified amino acid as defined above, and (b) a further antimicrobial agent as a combined preparation for separate, simultaneous or sequential use in the treatment or prevention of an antimicrobial infection.

In a yet further aspect the present invention provides a product comprising (a) a peptide, peptidomimetic or modified amino acid as defined above, and (b) a further antitumoural agent as a combined preparation for separate, simultaneous or sequential use in the treatment of tumour cells.

In a further aspect the present invention provides the use of a peptide, peptidomimetic or modified amino acid as defined above in the manufacture of a medicament for treating a microbial infection, preferably a bacterial infection.

In a further aspect the present invention provides the use of a peptide, peptidomimetic or modified amino acid as defined above in the manufacture of a medicament for treating tumour cells or preventing or reducing the growth, establishment spread, or metastasis of a tumour.

From amongst the above described class of molecule, there exists a novel group of highly effective molecules. These molecules are suitable for the various uses and methods described herein. Thus, in a further aspect, the present invention provides a peptide, peptidomimetic or (modified) amino acid having a net positive charge of at least +2 which incorporates a group of formula I:

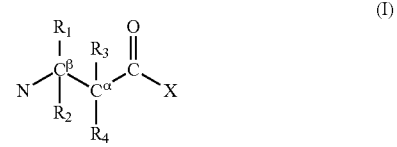

(I)

wherein any 2 from $R_1$, $R_2$, $R_3$ and $R_4$ are hydrogen atoms and 2 are substituting groups, which may be the same or different, comprise at least 7 non-hydrogen atoms, are lipophilic and include a cyclic group, said cyclic group not being attached directly either to the α or β carbon atom but optionally being linked or fused to a cyclic group in the other substituting group, where cyclic groups are fused the combined total number of non-hydrogen atoms for the two substituting groups is at least 12, and wherein X represents O, C, N or S, but excluding the compounds N-methyl-L-phenylalanyl-L-lysyl-L-prolyl-2,2-bis(phenylmethyl)-β-alanyl-D-Arginine and N-methyl-L-phenylalanyl-L-lysyl-L-prolyl-D-cyclohexylalanyl-2,2-bis(phenylmethyl)-β-alanyl-D-Arginine.

Using Chemical Abstracts type nomenclature rather than the IUPAC system the above two molecules would be called D-Arginine, N2-[N-[1-[N2-(N-methyl-L-phenylalanyl)-L-lysyl]-L-prolyl]-2,2-bis(phenylmethyl)-β-alanyl] and D-Arginine, N2-[N-[3-cyclohexyl-N-[1-[N2-(N-methyl-L-phenylalanyl)-L-lysyl]-L-prolyl]-D-alanyl]-2,2-bis(phenylmethyl)-β-alanyl] and their CAS nos. are 145149-42-4 and 145149-43-5 respectively.

The disclaimed compounds are disclosed in WO 92/12168 as anaphylatoxin receptor ligands useful in the treatment of inflammatory disease states, as such this document does not address the problem solved by the present invention.

It will be appreciated that the minimum figure of 12 for the combined total of non-hydrogen atoms in the two groups of $R_{1-4}$ when the cyclic groups of each moiety are fused is arrived at by adding the minimum number for the unfused groups (7+7=14) and subtracting 2 because two of the non-hydrogen atoms effectively participate in ring formation in each group. Preferably the combined total of non-hydrogen atoms in the two groups of $R_{1-4}$ when the cyclic groups of each moiety are fused is 14. Complex fused and linked groups can be envisaged where the two groups attached to the $C^\alpha$ or $C^\beta$ may contain more than one pair of fused cyclic groups, with or without additional linking bonds between the substituting groups. Nevertheless, the two substituting groups are preferably not fused or linked as molecules in which these groups have greatest flexibility of movement are preferred.

The nitrogen atom in the group of formula (I) is preferably not bound to any atom of groups $R_{1-4}$, except, of course, indirectly through $C^\beta$ or $C^\alpha$. Preferably the 5 atoms in the above backbone (N—$C^\beta$—$C^\alpha$—C—X) are connected to each other only in a linear, not cyclic, fashion. It will be appreciated that X and N in formula (I) have their normal valencies and thus will typically be further substituted as they are bound to other parts of the compound, e.g. further amino acids or N- or C-terminal capping groups.

The substituting groups of $R_{1-4}$ are generally lipophilic in nature and preferably carry no charge and preferably have no more than two, more preferably no more than one polar group. One or both of the substituting groups of $R_{1-4}$ preferably contain at least 8, more preferably at least 9 or 10 non-hydrogen atoms, e.g. 7-13, 7-12, 8-12 or 9-11 non-hydrogen atoms. These two substituting groups are preferably the same, if only for ease of synthesis. Preferably the two substituting groups are $R_1$ and $R_2$ or $R_3$ and $R_4$, $R_3$ and $R_4$ being most preferred.

As stated above, the cyclic groups of $R_{1-4}$ are not attached directly to either the α or β carbon atom because they are spaced therefrom by a chain of 1 to 4, preferably 1 to 3 atoms; these linking atoms may include nitrogen and/or oxygen but will typically be carbon atoms, preferably the linking atoms are unsubstituted. Preferred spacing moieties are shown in the Examples and form part of the substituting groups of $R_{1-4}$ as defined herein.

X may be substituted or unsubstituted and is preferably a N atom and preferably substituted. When X is N it may form part of an amide bond with a further amino acid, as shown in the molecules of Example 1. Alternatively, the N atom may be substituted, for example by an aminoalkyl group, e.g. aminoethyl or aminopropyl or dimethylaminoethyl, such molecules are shown in Example 2. In a further alternative the N atom may form part of a cyclic group such as piperazine, which may itself be substituted by alkyl or aminoalkyl groups, again as shown in Example 2.

The peptides or peptidominimetics incorporating a group of formula I will preferably have a modified C terminus, which is preferably amidated and is described above in relation to the molecules for use as cytolytic therapeutic agents.

Previous passages defining preferred substituting groups of the β amino acid apply, mutatis mutandis, to the two substituting groups of $R_{1-4}$. The peptides and peptidomimetics incorporating a group of formula I are a preferred sub-set of the molecules described earlier in this application as being for use as a cytolytic therapeutic agent and so all previous passages defining preferred characteristics of the molecules, for example their length and the other amino acids they contain, apply also to these molecules defined by their incorporation of a group of formula I, and vice versa. Particularly preferred molecules are 1 to 7 or 8 (e.g. 1 to 5), more preferably 1, 2, 3 or 4 amino acids in length. Peptidomimetic molecules will include the same number of subunits but these subunits will typically be linked by amide bond mimics; preferred linkages are discussed above and include esters and aminomethyl and ketomethylene.

The Examples herein show the structural motif of the present invention in the form of di-peptides (Example 1) and single modified amino acids and hepta-peptides (Examples 2 and 4). The molecules of the Examples represent preferred molecules of, and of use in, the present invention.

The peptides, peptidomimetics and amino acids of the invention may be in salt form, cyclic or esterified, as well as the preferred amidated derivatives discussed above.

A preferred class of molecules of, and of use in, the present invention are β, preferably $\beta^{2,2}$-amino acid derivatives which have a single $\beta^{2,2}$-amino acid incorporating two lipophilic side chains as defined above, the di-substituted β-amino acid being flanked by two cationic groups. As described previously, the two substituting groups are preferably the same, include a 6 membered cyclic group and at least 8, preferably at least 10 non-hydrogen atoms. These molecules are particularly suitable as antimicrobial agents and are suitable for oral administration.

The molecules described herein may be synthesised in any convenient way. Generally the reactive groups present (for example amino, thiol and/or carboxyl) will be protected during overall synthesis. The final step in the synthesis will thus be the deprotection of a protected derivative of the invention. Methods of compound synthesis constitute a further aspect of the present invention. For example, in one embodiment is provided a method of synthesising a peptide, peptidomimetic or modified amino acid having a net positive charge of at least +2 which incorporates a group of formula I as defined herein, which method includes the removal of a protecting group from said peptide, peptidomimetic or modified amino acid.

In building up the peptide, one can in principle start either at the C-terminal or the N-terminal although the C-terminal starting procedure is preferred.

Methods of peptide synthesis are well known in the art but for the present invention it may be particularly convenient to carry out the synthesis on a solid phase support, such supports being well known in the art.

A wide choice of protecting groups for amino acids are known and suitable amine protecting groups may include carbobenzyloxy (also designated Z) t-butoxycarbonyl (also designated Boc), 4-methoxy-2,3,6-trimethylbenzene sulphonyl (Mtr) and 9-fluorenylmethoxy-carbonyl (also designated Fmoc). It will be appreciated that when the peptide is built up from the C-terminal end, an amine-protecting group will be present on the α-amino group of each new residue added and will need to be removed selectively prior to the next coupling step.

Carboxyl protecting groups which may, for example be employed include readily cleaved ester groups such as benzyl (Bzl), p-nitrobenzyl (ONb), or t-butyl (OtBu) groups as well as the coupling groups on solid supports, for example the Rink amide linked to polystyrene.

Thiol protecting groups include p-methoxybenzyl (Mob), trityl (Trt) and acetamidomethyl (Acm).

Preferred peptides of the invention may conveniently be prepared using the t-butyloxycarbonyl (Boc) protecting group for the amine side chains of Lys, Orn, Dab and Dap as well as for protection of the indole nitrogen of the tryptophan residues. Fmoc can be used for protection of the alpha-amino groups. For peptides containing Arg, 2,2,4,6,7-pentamethyldihydrobenzofurane-5-sulfonyl can be used for protection of the guanidine side chain.

A wide range of procedures exists for removing amine- and carboxyl-protecting groups. These must, however, be consistent with the synthetic strategy employed. The side chain protecting groups must be stable to the conditions used to remove the temporary α-amino protecting group prior to the next coupling step.

Amine protecting groups such as Boc and carboxyl protecting groups such as tBu may be removed simultaneously by acid treatment, for example with trifluoroacetic acid. Thiol protecting groups such as Trt may be removed selectively using an oxidation agent such as iodine.

References and techniques for synthesising peptidomimetic compounds are provided above and known to the skilled man.

Formulations comprising one or more compounds of the invention in admixture with a suitable diluent, carrier or excipient constitute a further aspect of the present invention. Such formulations may be for, inter alia, pharmaceutical (including veterinary) purposes and thus a suitable diluent, carrier or excipient will preferably be pharmaceutically acceptable. Suitable diluents, excipients and carriers are known to the skilled man.

The molecules described herein are cytolytic in nature and are of particular utility as antimicrobial, e.g. antibacterial or antifungal agents, antibacterial uses being preferred. The specificity of the molecules also makes them suitable as antitumoural agents. Thus in a further aspect the present invention provides a peptide, peptidomimetic or (modified) amino acid having a net positive charge of at least +2 which incorporates a group of formula I:

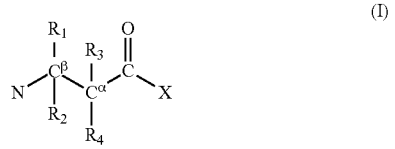

wherein any 2 from $R_1$, $R_2$, $R_3$ and $R_4$ are hydrogen atoms and 2 are substituting groups, which may be the same or different, comprise at least 7 non-hydrogen atoms, are lipophilic and include a cyclic group, said cyclic group not being attached directly either to the α or β carbon atom but optionally being linked or fused to a cyclic group in the other substituting group, where cyclic groups are fused the combined total number of non-hydrogen atoms for the two substituting groups is at least 12, and wherein X represents O, C, N or S, but excluding the compounds N-methyl-L-phenylalanyl-L-lysyl-L-prolyl-2,2-bis(phenylmethyl)-β-alanyl-D-Arginine and N-methyl-L-phenylalanyl-L-lysyl-L-prolyl-D-cyclohexylalanyl-2,2-bis(phenylmethyl)-β-alanyl-D-Arginine, for use in therapy.

The invention further provides a peptide, peptidomimetic or modified amino acid having a net positive charge of at least +2 which incorporates a group of formula I:

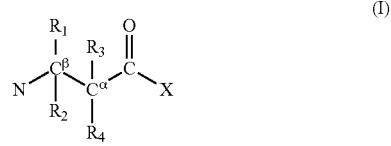

wherein any 2 from $R_1$, $R_2$, $R_3$ and $R_4$ are hydrogen atoms and 2 are substituting groups, which may be the same or different, comprise at least 7 non-hydrogen atoms, are lipophilic and include a cyclic group, said cyclic group not being attached directly either to the α or β carbon atom but optionally being linked or fused to a cyclic group in the other substituting group, where cyclic groups are fused the combined total number of non-hydrogen atoms for the two substituting groups is at least 12, and wherein X represents O, C, N or S, for use as a cytolytic therapeutic agent. Preferably the uses are as antimicrobial, especially antibacterial agents, or as antitumoural agents.

In a further aspect the present invention provides a method of treating or preventing a microbial infection, preferably a bacterial infection, which method comprises administration to a subject of a peptide, peptidomimetic or modified amino acid as defined above.

In a further aspect the present invention provides a method of treating tumour cells or preventing or reducing the growth, establishment spread, or metastasis of a tumour, which method comprises administration to a subject of a peptide, peptidomimetic or modified amino acid as defined above.

In a further aspect the present invention provides the use of a peptide, peptidomimetic or modified amino acid as defined above in the manufacture of a medicament for treating a microbial infection, preferably a bacterial infection.

In a further aspect the present invention provides the use of a peptide, peptidomimetic or modified amino acid as defined above in the manufacture of a medicament for treating tumour cells or preventing or reducing the growth, establishment spread, or metastasis of a tumour.

The microbial infection may be or may be suspected of being a multipathogen infection, and the treatment of such infections (e.g. at the site of a chronic wound), for example of infections comprising both Gram positive and Gram negative bacterial species, represent preferred targets for uses and methods according to the present invention.

The amount administered should be effective to kill all or a proportion of the target cells or to prevent or reduce their rate of multiplication, or to inhibit metastasis or otherwise to lessen the harmful effect of the tumour on the patient. The clinician or patient should observe improvement in one or more of the parameters or symptoms associated with the tumour. Administration may also be prophylactic. The patient will typically be a human patient but non-human animals, such as domestic or livestock animals may also be treated.

Unlike the majority of agents which have protein targets, the molecules of the present invention can target a wide variety of cancers. Preferred cancer targets include lymphomas, leukemias, neuroblastomas and glioblastomas (e.g. from the brain), carcinomas and adenocarcinomas (particularly from the breast, colon, kidney, liver, lung, ovary, pancreas, prostate and skin) and melanomas.

The compositions according to the invention may be presented, for example, in a form suitable for oral, topical, nasal, parenteral, intravenal, intratumoral, rectal or regional (e.g. isolated limb perfusion) administration. Administration is typically by a parenteral route, preferably by injection subcutaneously, intramuscularly, intracapsularly, intraspinaly, intratumouraly or intravenously.

The active compounds defined herein may be presented in the conventional pharmacological forms of administration, such as tablets, coated tablets, nasal sprays, solutions, emulsions, liposomes, powders, capsules or sustained release forms. Conventional pharmaceutical excipients as well as the usual methods of production may be employed for the preparation of these forms.

Organ specific carrier systems may also be used.

Injection solutions may, for example, be produced in the conventional manner, such as by the addition of preservation agents, such as p-hydroxybenzoates, or stabilizers, such as EDTA. The solutions are then filled into injection vials or ampoules.

Preferred formulations are those in which the peptides are dissolved in saline. Such formulations being suitable for use in preferred methods of administration, especially local administration, i.e. intratumoural, e.g. by injection or by perfusion/infusion of a preferably isolated (including partial isolation) limb, body region or organ.

Dosage units containing the active molecules preferably contain 0.1-10 mg, for example 1-5 mg of the antitumour agent. The pharmaceutical compositions may additionally comprise further active ingredients, including other cytotoxic agents such as other antitumour peptides. Other active ingredients may include different types of cytokines e.g. IFN-γ, TNF, CSF and growth factors, immunomodulators, chemotherapeutics e.g. cisplatin or antibodies or cancer vaccines.

In employing such compositions systemically, the active molecule is present in an amount to achieve a serum level of the bioactive molecule of at least about 5 μg/ml. In general, the serum level need not exceed 500 μg/ml. A preferred serum level is about 100 μg/ml. Such serum levels may be achieved by incorporating the bioactive molecule in a composition to be administered systemically at a dose of from 1 to about 10 mg/kg. In general, the molecule(s) need not be administered at a dose exceeding 100 mg/kg.

In a further aspect the present invention provides a product comprising (a) a peptide, peptidomimetic or modified amino acid having a net positive charge of at least +2 and incorporating a group of formula (I) as defined herein, and (b) a further antimicrobial agent as a combined preparation for separate, simultaneous or sequential use in the treatment or prevention of an antimicrobial infection.

In a yet further aspect the present invention provides a product comprising (a) a peptide, peptidomimetic or modified amino acid having a net positive charge of at least +2 and incorporating a group of formula (I) as defined herein and (b) a further antitumoural agent as a combined preparation for separate, simultaneous or sequential use in the treatment of tumour cells.

Compounds of the invention and compounds suitable for the methods and uses of the invention include salt forms and appropriate pharmaceutically acceptable salts for peptides and similar molecules are well known to those skilled in the art.

The invention is further described in the following Examples, which includes some reference molecules outside the scope of the present invention, and with reference to the figures in which.

Figure 4:
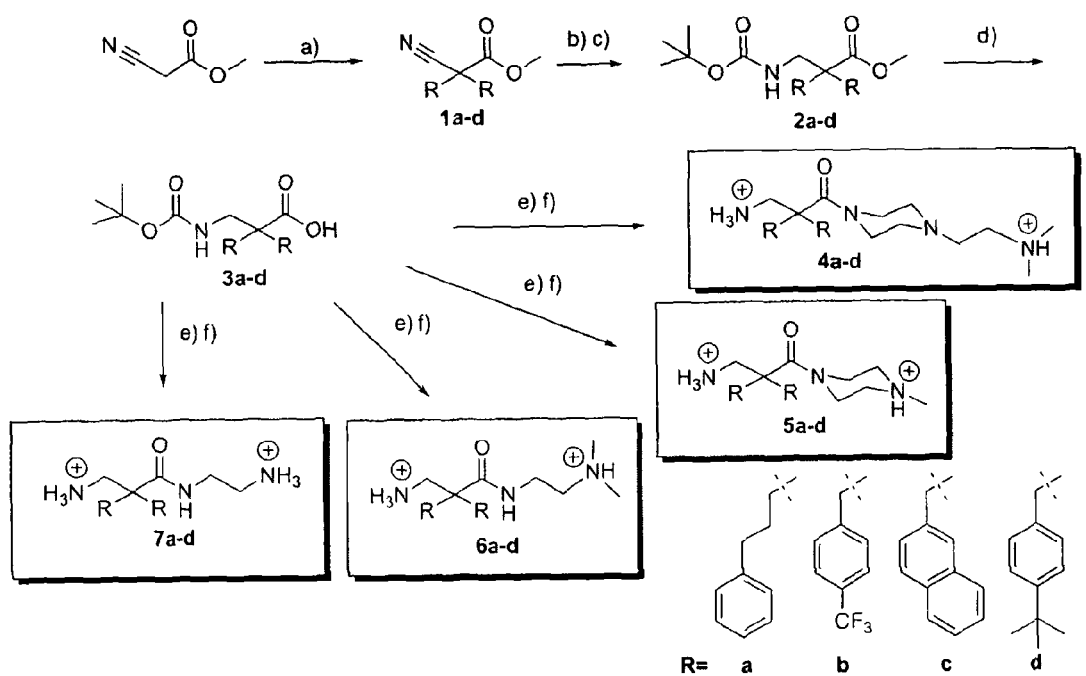

FIG. 4 shows a schematic overview of the synthesis of the compounds of Example 4. a) NaOMe (1 eq.), R—Br (1 eq.), performed twice, 78° C. s: MeOH. b) Ra/Ni, H2(g), 45° C., 5 days, s: MeOH containing 2% acetic acid. c) TEA, pH 8, Boc$_2$O (1.2 eq.), r.t, 18 h, s: H2O:dioxane (1:5). d) LiOH (6 eq.), 18 h, 100° C., s: H$_2$O:dioxane (1:3). e) DIPEA (3 eq.), TFFH (1.5 eq.), r.t, 2 h, then addition of the desired amine (2 eq.), up to 7 days, s: DMF. f) TFA:TIS:H$_2$O (95:2.5:2.5), r.t, 2 h, s: DCM. All β$^{2,2}$-amino acid derivatives were isolated as their di-trifluoroacetate salts.

EXAMPLES

Example 1

Figure 1:
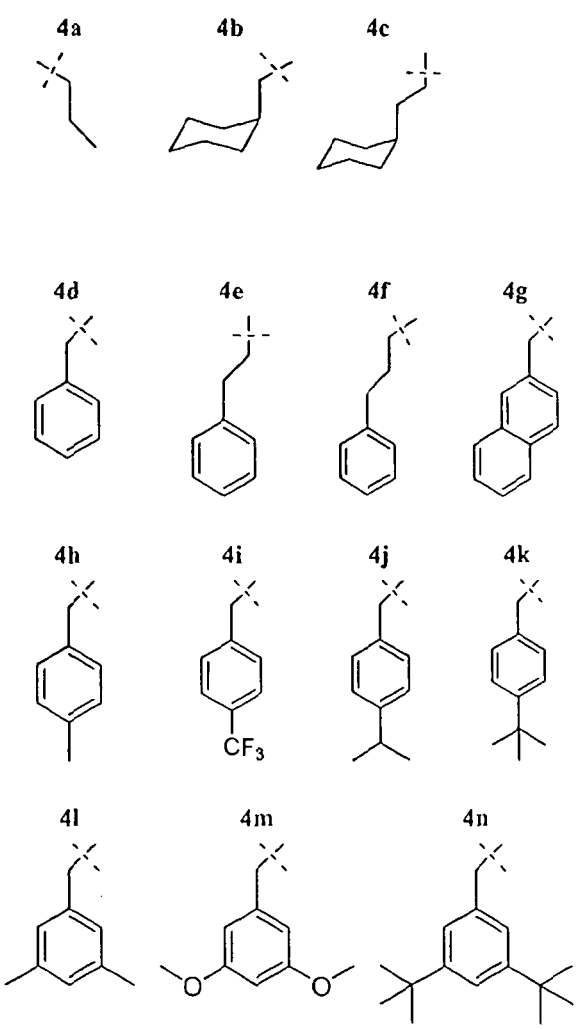
FIG. 1 shows compounds 4a-n of Example 1.
Figure 2:
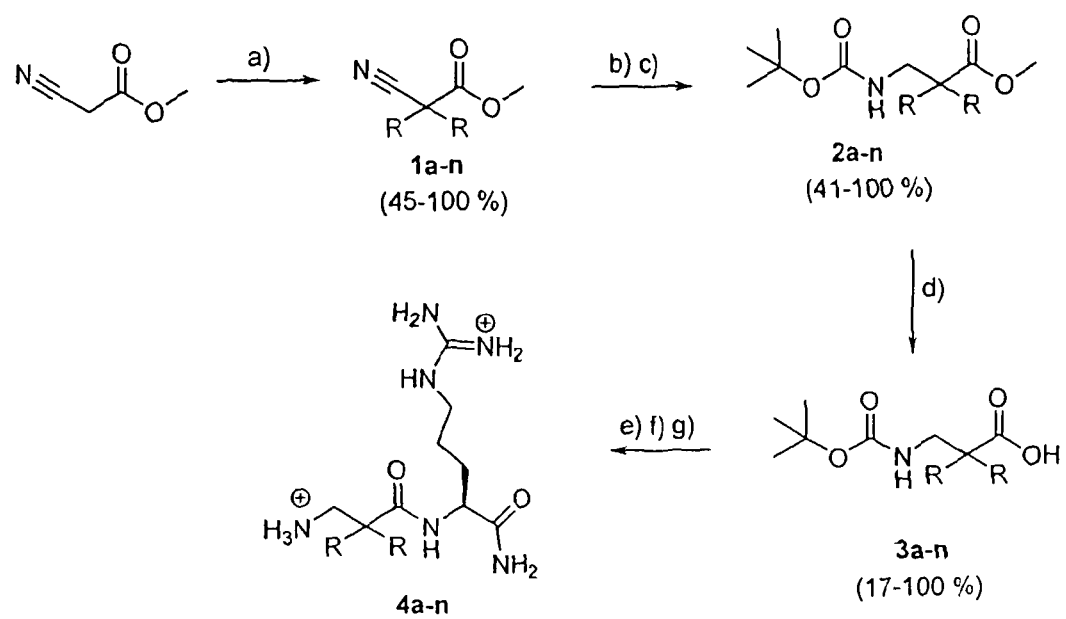
FIG. 2 shows a schematic overview of the synthesis of compounds 4a-n as described in Example 1.

A series of molecules based on the scaffold of an achiral lipophilic 3-amino-2,2-disubstituted propionic acid (β$^{2,2}$-amino acid) coupled to a C-terminal L-arginine amide residue were generated and tested for their antimicrobial activity. These di-peptides have the side-chain functionalities of a tri-peptide due to the β$^{2,2}$-amino acid derivative. A wide range of lipophilic substituents of the β$^{2,2}$-amino acid derivative was explored as shown in FIG. 1. An overview of the synthesis of compounds 4a-n is presented in FIG. 2.

Reagents and Analytical Methods $^1$H and $^{13}$C NMR spectra were recorded on 400 or 600 MHz Varian spectrometers. Mass spectra were obtained on a Micromass Quattro LC (Micromass, Manchester, UK). High resolution mass spectra were obtained on a Waters Micromass LCT Premier (Micromass, Manchester, UK). Commercially available compounds and solvents were purchased from Sigma-Aldrich and used without further purification. Preparative RP-HPLC was carried out on a Waters system equipped with a RP BondaPak C18 125 Å, 10 μm, 25×100 mm, and eluted with acetonitrile and water, both containing 0.1% TFA. Analytical HPLC was carried out on a Waters 2695 HPLC equipped with a RP-HPLC Delta Pak C18, 100 Å, 5 μm, 3.9×150 mm Waters column and analyzed at wavelength 214 nm with PDA detector spanning from wavelength 210 to 310 nm. All compounds were prepared by using parallel reaction carousels from Radleys®.

General Procedure for Dialkylation of Methyl Cyanoacetate (GP1) 1a-n.

Sodium methoxide (20 mmol) was dissolved in methanol (0.2 M) and methyl cyanoacetate (20 mmol) was added. After 5 min stirring at r.t. the desired benzyl bromide (20 mmol) was added and the solution was heated to reflux. After 15 min the solution was cooled to r.t. A second portion of sodium methoxide (20 mmol) was added and after 5 min stirring at r.t. the second portion of the desired benzyl bromide (20 mmol) was added once more followed by 15 min reflux. The volume of the reaction mixture was reduced to about ⅓ under vacuum and extracted with water/ethyl acetate. The organic phase was dried over MgSO4 and evaporated to dryness. The product was used in following synthesis without any further purification.

General Procedure for Reduction of Nitriles to Amines with Ra/Ni and Following Boc-Protection (GP2) 2a-n.

Ra/Ni (approximate 2 ml/g nitrile) was washed 3 times with methanol under argon before the desired nitrile (3.5 mmol) dissolved in methanol (0.1 M) was added along with acetic acid (approximately 1 ml/g nitrite). The reaction mixture was hydrogenated at 45° C. for 5 days under 1 bar $H_2$ pressure. Afterwards the reaction mixture was filtered through CELITE (diatomite) to remove the Ra/Ni before it was evaporated to dryness. The crude $\beta^{2,2}$-amino acid methyl ester (0.35 mmol) was dissolved in a mixture of 1,4-dioxane and water 5:1 (~0.35 M) and pH was adjusted to 8 with TEA, and $Boc_2O$ (0.42 mmol) dissolved in as little as possible 1,4-dioxane was added. The solution was stirred at r.t. for about 18 h before it was acidified to pH 2-3 with 10% citric acid and extracted 3 times with ethyl acetate. The organic phase was dried over $MgSO_4$ and evaporated to dryness. The product was used in following synthesis without any further purification.

General Procedure for Esterhydrolysis (GP3) 3a-n.

The Boc-protected $\beta^{2,2}$-amino acid methyl ester (0.35 mmol) was dissolved in a mixture of 1,4-dioxane and water 3:1 (1.17 mM) and lithium hydroxide (2.1 mmol) dissolved in as little water as possible was added. The reaction mixture was stirred at reflux under $N_2$ for 18 h before the volume was reduced to approximately ⅕ under vacuum. Water (10 ml) was added to the reaction mixture and pH was adjusted drop wise to 1-2 with 0.1 M HCl. This aqueous solution was extracted 3 times with equal volume of ethyl acetate. The organic phase was dried over $MgSO_4$ and evaporated to dryness. The product was used in following synthesis without any further purification.

General Procedure for L-Arginine Coupling of Boc-Protected $\beta^{2,2}$-Amino Acids (GP4) 4 a-n.

The Boc-protected $\beta^{2,2}$-amino acid (0.2 mmol) was dissolved in DMF (0.02 M) and DIPEA (0.6 mmol) was added along with TFFH (0.2 mmol). The amino acid was preactivated for 2 h before H-Arg-$NH_2 \times 2HCl$ (0.3 mmol) was added. The reaction mixture was stirred at r.t for 7 days before it was diluted with ethyl acetate and washed with brine. The organic phase was dried over $MgSO_4$ and evaporated to dryness. The crude Boc-protected product was deprotected by dissolving it in DCM (~0.4 M) and adding a volume equivalent of TFA:TIS:Water (95:2.5:2.5). The mixture was stirred at r.t. for 2 h before it was evaporated to dryness. The crude product was purified by preparative RP-HPLC. The purity of the peptides was checked by analytical RP-HPLC before the solution was evaporated to dryness, and residue was redissolved in water and lyophilised. All compounds possessed purity above 95%.

Cell Testing

The antimicrobial testing was conducted by TosLab A/S (Tromsø, Norway). Each compound was diluted to 1 mg/ml in water and tested in duplicates at 200, 100, 50, 35, 15, 10, 5, 2.5, 1, 0.5 µg/ml except 4n which was tested at 50, 35, 15, 10, 5, 2.5, 1, 0.5 µg/ml due to solubility problems. All tested compounds were di TFA salts.

The bacterial strains were grown in 2% Bacto Peptone water until exponential growth was achieved. The MIC was determined by overnight incubation in 1% Bacto Peptone water at 37° C. A bacterial concentration of $2 \times 10^6$ cfu/ml was used. Both negative control (no peptide) and positive control (Gentamicin) was used for all bacterial strains. Growth or no growth was judged by the turbidity of the wells. MBC was determined by plating on agar plates all concentrations at and above the MIC value, incubating at 37° C. over night and determining growth or no growth.

All compounds displaying MIC values less than 50 µg/ml were retested using the same procedure.

MIC and MBC values are shown in Tables 1A and B.

The hemolytic testing against human erythrocytes was conducted by Lytix Biopharma A/S (Tromso, Norway). Each compound was tested from a concentration of 1 mg/ml and lower, except 4k and 4n which was only tested up to 0.5 mg/ml due to solubility problems. 8 mL of blood was collected from adult healthy male donors. The blood was divided equally and distributed in a commercial available EDTA containing test tube (BD vacutainer, 7.2 mg $K_2$ EDTA) and in a 10 mL reaction vial containing 40 µL of a heparin solution (1000 U/mL in 0.9% sodium chloride). After 30 minutes the hematocrit of the EDTA treated blood was determined. The heparinized blood was centrifuged for 10 minutes at 1500 rpm and the supernatant removed. Subsequently the RBCs were washed with prewarmed PBS three times, and diluted to 10% hematocrit. The compounds dissolved in PBS (concentration 1 µg/mL to 1000 .mu.g/mL) and the erythrocytes were incubated under agitation at 37° C. for one hour. A positive control with an end concentration of 0.1% TRITON X-100 (nonionic surfactant) and a negative control containing pure PBS buffer were included. The samples were centrifuged (4000 rpm) for 5 minutes and the absorption of the supernatant was measured at 405 nm. The values given in Table 1A correspond to 50% hemolysis.

Stability Against α-Chymotrypsin

The stability testing against α-chymotrypsin was conducted by dissolving the desired compounds to 1 mg/ml in water. α-Chymotrypsin was dissolved to 0.1 mg/ml in 1 mM HCl containing 2 mM CaCl2. The enzymatic digestion was performed in 100 mM TRIS HCl containing 10 mM $CaCl_2$. Final enzyme concentration was 2 µg/ml, and final peptide concentration was 100 µg/ml. Total volume was 0.5 ml.

15 µl samples were collected at 0, 15, 30, 60, 120 and 240 min in addition to the 24 and 48 hours samples. To the samples it was added an external standard (atenolol hydrochloride) and 100 µl 10% acetic acid to terminate digestion before it was diluted to 1 ml with water.

For every test there were done a negative control without enzyme to ensure that degradation was due to enzyme activity and not other factors. Succinyl-ala-ala-pro-phe-para nitroanhiine was used as positive control. All test were run in triplicates.

Results

TABLE 1A

Minimum inhibitory concentration (MIC) against S. aureus, MRSA, MRSE and E. coli and EC50 values against human RBC for antimicrobial dipeptides prepared in the study.

| Compound | MIC$^a$ (µM) | | | | $EC_{50}{}^b$ (µM) |
| | S. aureus$^c$ | MRSA$^d$ | MRSE$^e$ | E. coli$^f$ | RBC$^g$ |
|---|---|---|---|---|---|
| 4a | — | — | — | — | — |
| 4b | 150 | 150 | 75 | — | — |
| 4c | 7.2 | 7.2 | 7.2 | 144 | — |
| 4d | — | — | — | — | n.t. |
| 4e | 147 | 147 | 74 | — | — |
| 4f | 49 | 49 | 35 | — | — |
| 4g | 6.6 | 5.0 | 6.6 | 266 | 470 |
| 4h | 147 | 74 | 74 | — | — |
| 4i | 12.7 | 3.2 | 12.7 | 254 | n.t. |
| 4j | 10.2 | 6.8 | 6.8 | 136 | 386 |
| 4k | 6.5 | 3.3 | 5.0 | 46 | — |

TABLE 1A-continued

Minimum inhibitory concentration (MIC) against *S. aureus*, MRSA, MRSE and *E. coli* and EC50 values against human RBC for antimicrobial dipeptides prepared in the study.

| Compound | MIC$^a$ (μM) | | | | EC$_{50}$$^b$ (μM) |
|---|---|---|---|---|---|
| | *S. aureus*$^c$ | MRSA$^d$ | MRSE$^e$ | *E. coli*$^f$ | RBC$^g$ |
| 4l | 60 | 49 | 35 | — | — |
| 4m | 259 | 259 | 129 | — | — |
| 4n | 2.9 | 2.1 | 10.1 | 5.7 | 99 |

$^a$Highest concentration tested was 200 μg/ml.
$^b$Highest concentration tested was 1000 μg/ml.
$^c$*Staphylococcus aureus* (ATCC 25923),
$^d$methicillin resistant *Staphylococcus aureus* (ATCC 33591),
$^e$methicillin resistant *Staphylococcus epidermidis* (ATCC 27626),
$^f$*Escherichia coli* (ATTC 25922) and
$^g$human red blood cells.
The notation "—"denotes no detectable activity (MIC or EC50) within the concentration range tested.
n.t: not tested.

TABLE 1B

Minimum bactericidal concentration (MBC) against *S. aureus*, MRSA, MRSE and *E. coli*. The strains are the same as for those represented in Table 1A above.

| Compound | MBC$^e$ (μM) | | | |
|---|---|---|---|---|
| | *S. aureus*$^a$ | MRSA$^b$ | MRSE$^c$ | *E. coli*$^d$ |
| 4a | >360 | >360 | >360 | >360 |
| 4b | 301 | 150 | 75 | >301 |
| 4c | 7.2 | 7.2 | 7.2 | 289 |
| 4d | >307 | >307 | >307 | >307 |
| 4e | 147 | 147 | 74 | >294 |
| 4f | 49 | 49 | 49 | >282 |
| 4g | 6.6 | 5.3 | 6.6 | 266 |
| 4h | 147 | 110 | 110 | >294 |
| 4i | 12.7 | 6.3 | 12.7 | >254 |
| 4j | 6.8 | 6.8 | 6.8 | 136 |
| 4k | 6.5 | 6.5 | 5.2 | 46 |
| 4l | 49 | 49 | 21 | >282 |
| 4m | >259 | 259 | 129 | >259 |
| 4n | 4.6 | 4.6 | 3.4 | 5.7 |

A selection of six compounds (4c, 4g, 4h, 4i, 4k and 4m) was investigated for proteolytic stability against α-chymotrypsin. The results revealed that no degradation could be detected for any of the compounds over a period of 48 hours. We also found that all test-compounds were chemically stable in aqueous solutions at pH 7.4 for at least 48 hours.

The results demonstrated a strong correlation between antimicrobial potency and overall lipophilicity of the compounds prepared. This can be illustrated by a comparison between the potency of the compounds against *S. aureus* and their retention time (Rt) on an analytical RP-HPLC C18-column, which demonstrated the affinity of the compounds for the hydrophobic stationary phase of the column (results not shown).

Haemolytic activity of the compounds prepared was used as a measurement of toxicity, and with the exception of compounds 4g, 4j and 4n, the compounds were non-haemolytic within the concentration range tested (<1000 μg/ml). Highest haemolytic activity was displayed by compound 4n, but the EC$_{50}$ concentration was nevertheless ten to almost 50 times higher than the MIC values against both the Gram-positive and Gram-negative bacteria. It was noteworthy that compounds 4j and 4k, which displayed similar antimicrobial potency, were quite different with respect to haemolytic activity. This indicated that haemolytic activity and antimicrobial potency were not determined by the exact same structural properties.

Example 2

Further molecules of the invention were made and tested both for antibacterial and anti-cancer activity.
Materials and Methods
Bacterial Strains
*Staphylococcus aureus* (ATTC 25923)
Methicillin resistant *Staphylococcus aureus* (ATCC 33591)
Methicillin resistant *Staphylococcus epidermidis* (ATCC 27626)
*Escherichia coli* (ATTC 25922)
Cancer Cell Lines
A20 or MethA
Cells for Toxicity Studies Used
MRC-5 and human RBC
Highest Concentrations Tested in the Various Assays were
Antimicrobial assays: 200 μg/ml
Anticancer assays: 500 μg/ml
MRC-5 assay: 500 μg/ml
RBC assay: 1000 μg/ml
CHEMDRAW ULTRA VERSION 11.0 (chemical drawing software) was used for calculating the physiochemical properties Log P, tPSA and CLogP.
Synthesis of Molecules Swelling of resin: The Rink amide MBHA resin (0.64 mmol/g loading) was swelled in 7 ml DMF for 1 hour before it was washed five times with 7 ml DMF.

Fmoc-removal: 7 ml 20% piperidine in DMF was added to the reaction tubes and the suspension was stirred for 10 min before the solution was removed. This procedure was repeated twice with stirring times of 1 min before the resin was washed five times with 7 ml DMF.

Coupling of amino acids to the deprotected resin: Fmoc-Lys(Boc)-OH or Fmoc-Trp(Boc)-OH (4 equiv.), HOBt hydrate (4 equiv.) and HBTU (3.92 equiv.) was dissolved in 5 ml DMF, DIPEA (8 equiv.) was added and the mixture was allowed to preactivate for 15 minutes before it was added to the resin. After stirring for 1 hour the coupling mixture was removed and the resin was washed five times with 7 ml DMF.

Coupling of the β-amino acid to the deprotected resin: Fmoc-β-aa-OH (2 equiv.) and TFFH (1.96 equiv.) was dissolved in 5 ml DMF, DIPEA (8 equiv.) was added and the mixture was allowed to preactivate for 15 minutes before it was added to the resin. After stirring for 48 hours the coupling mixture was removed and the resin was washed five times with 7 ml DMF.

Coupling of the amino acid after the β-amino acid to the deprotected resin: Fmoc-Trp(Boc)-OH (4 equiv.) and TFFH (3.92 equiv.) was dissolved in 5 ml DMF, DIPEA (8 equiv.) was added and the mixture was allowed to preactivate for 15 minutes before it was added to the resin. After stirring for 24 hours the coupling mixture was removed and the resin was washed five times with 7 ml DMF.

After the last coupling, the resin was washed five times with DCM before it was allowed to air-dry over night.

Cleavage from the resin and Boc-removal: 10 ml TFA:TIS:water 95:2.5:2.5 was added to the reaction tubes and the suspension was stirred for 2 hours before the peptide solution was collected. This procedure was repeated twice with stirring times of 10 minutes. The collected peptide solutions were evaporated to dryness under reduced pressure, precipitated with diethyl ether and washed with diethyl ether. The peptides were purified by HPLC and lyophilized.

Cell Testing
Suitable methodologies are described in Example 1.
Results

TABLE 2

Biological potency of β2,2-amino acid 1,2-diamino ethane derivatives. (All values in µg/ml).

|  | 1 | 2 | 3 |
|---|---|---|---|
| IUPAC-Name | N-(2-aminoethyl)-2-(aminomethyl)-2-propyl-pentanamide<br>Log P: 0.53<br>tPSA: 81.14<br>CLogP: 1.24 | 3-amino-N-(2-aminoethyl)-2,2-bis(cyclohexylmethyl)propanamide<br>Log P: 2.7<br>tPSA: 81.14<br>CLogP: 4.424 | N-(2-aminoethyl)-2-(aminomethyl)-4-cyclohexyl-2-(2-cyclohexylethyl)butanamide<br>Log P: 3.54<br>tPSA: 81.14<br>CLogP: 5.482 |
| Formula | $C_{11}H_{25}N_3O$ | $C_{19}H_{37}N_3O$ | $C_{21}H_{41}N_3O$ |
| Mw | Exact Mass: 215.1998<br>Molecular Weight: 215.3357 | Exact Mass: 323.2937<br>Molecular Weight: 323.5166 | Exact Mass: 351.3250<br>Molecular Weight: 351.5697 |
| Antimicrobial potency (MIC) | | | |
| *S. aureus* | >200 | 200 | 7.5/10 |
| MRSA | >200 | 100 | 5/15 |
| MRSE | >200 | 35 | 2.5/5 |
| *E. coli* | >200 | >200 | 15/10 |
| Anticancer potency ($IC_{50}$) | | | |
| A20 | n.t. | n.t. | <3.35/<3.35/1.7 |
| MethA | n.t. | n.t. | n.t. |
| Toxicity | | | |
| MRC-5 | n.t. | 18.5 | <10/<10 |
| RBC ($EC_{50}$) | n.t. | >1000 | 62* |
| Anti-Cancer Selectivity | | | |
| MRC-5/A20 | n.t. | n.t. | (<5.9) |
| RBC/A20 | n.t. | n.t. | 36.5 |

|  | 4 | 5 | 6 |
|---|---|---|---|
| IUPAC-name | 3-amino-N-(2-(aminoethyl)-2,2-dibenzyl-propanamide<br>Log P: 2.08<br>tPSA: 81.14<br>CLogP: 2.11 | N-(2-aminoethyl)-2-(aminomethyl)-2-phenethyl-4-phenylbutanamide<br>Log P: 2.91<br>tPSA: 81.14<br>CLogP: 3.018 | N-(2-aminoethyl)-2-(aminomethyl)-5-phenyl-2-(3-phenylpropyl)pentanamide<br>Log P: 3.75<br>tPSA: 81.14<br>CLogP: 4.076 |
| Formula | $C_{19}H_{25}N_3O$ | $C_{21}H_{29}N_3O$ | $C_{23}H_{33}N_3O$ |
| Mw | Exact Mass: 311.1998<br>Molecular Weight: 311.4213 | Exact Mass: 339.2311<br>Molecular Weight: 339.4745 | Exact Mass: 367.2624<br>Molecular Weight: 367.5276 |
| Antimicrobial potency (MIC) | | | |
| *S. aureus* | >200 | 100 | 35/50 |
| MRSA | >200 | 100 | 35 |

TABLE 2-continued

Biological potency of β2,2-amino acid 1,2-diamino ethane derivatives. (All values in μg/ml).

| | | | |
|---|---|---|---|
| MRSE | >200 | 50 | 15 |
| E. coli | >200 | >200 | 200 |
| Anticancer potency (IC$_{50}$) | | | |
| A20 | 68.6 | n.t. | 8.3 |
| MethA | n.t. | n.t. | n.t. |
| Toxicity | | | |
| MRC-5 | 261 | 21.5 | 35 |
| RBC (EC$_{50}$) | >1000 | >1000 | 820 |
| Anti-Cancer Selectivity | | | |
| MRC-5/A20 | 3.8 | n.t. | 4.2 |
| RBC/A20 | n.t. | n.t. | 98.8 |

| | 7 | 8 | 9 |
|---|---|---|---|
| IUPAC-name | 3-amino-N-(2-aminoethyl)-2,2-bis(naphthalen-2-ylmethyl)propanamide | 3-amino-N-(2-aminoethyl)-2,2-bis(4-methylbenzyl)propanamide | 3-amino-N-(2-aminoethyl)-2,2-bis(4-(trifluoromethyl)benzyl)propanamide |
| | LogP: 4.07 | Log P: 3.05 | Log P: 3.92 |
| | tPSA: 81.14 | tPSA: 81.14 | tPSA: 81.14 |
| | CLogP: 4.458 | CLogP: 3.108 | CLogP: 3.876 |
| Formula | C$_{27}$H$_{29}$N$_3$O | C$_{21}$H$_{29}$N$_3$O | C$_{21}$H$_{23}$F$_6$N$_3$O |
| Mw | Exact Mass: 411.2311 | Exact Mass: 339.2311 | Exact Mass: 447.1745 |
| | Molecular Weight: 411.5387 | Molecular Weight: 339.4745 | Molecular Weight: 447.4172 |
| Antimicrobial potency (MIC) | | | |
| S. aureus | 2.5/5 | 200 | 10 |
| MRSA | 5 | 100 | 5 |
| MRSE | 2.5/5 | 100 | 10 |
| E. coli | 15 | >200 | 35 |
| Anticancer potency (IC$_{50}$) | | | |
| A20 | <3.35/0.7* | n.t. | <5/1.0* |
| MethA | n.t. | n.t. | n.t. |
| Toxicity | | | |
| MRC-5 | 13.5/14 | 26/44 | <10/12 |
| RBC (EC$_{50}$) | 292* | >1000 | 287 |
| Anti-Cancer Selectivity | | | |
| MRC-5/A20 | 19.3-20 | n.t. | 10-12 |
| RBC/A20 | 417 | n.t. | 287 |

10  11  12

TABLE 2-continued

Biological potency of β2,2-amino acid 1,2-diamino ethane derivatives. (All values in μg/ml).

| | | | |
|---|---|---|---|
| IUPAC-name | 3-amino-N-(2-aminoethyl)-2,2-bis(4-isopropylbenzyl)propanamide<br>Log P: 4.55<br>tPSA: 81.14<br>CLogP: 4.964 | 3-amino-N-(2-aminoethyl)-2,2-bis(4-tert-butylbenzyl)propanamide<br>Log P: 5.49<br>tPSA: 81.14<br>CLogP: 5.762 | 3-amino-N-(2-aminoethyl)-2,2-bis(3,5-dimethylbenzyl)propanamide<br>Log P: 4.02<br>tPSA: 81.14<br>CLogP: 4.106 |
| Formula<br>Mw | $C_{25}H_{37}N_3O$<br>Exact Mass: 395.2937<br>Molecular Weight: 395.5808 | $C_{27}H_{41}N_3O$<br>Exact Mass: 423.3250<br>Molecular Weight: 423.6339 | $C_{23}H_{33}N_3O$<br>Exact Mass: 367.2624<br>Molecular Weight: 367.5276 |
| Antimicrobial potency (MIC) | | | |
| S. aureus | 5/10 | 2.5 | 35 |
| MRSA | 5/10 | 2.5 | 35 |
| MRSE | 5 | 2.5 | 5/10 |
| E. coli | 12.5/35 | 5 | 50/100 |
| Anticancer potency ($IC_{50}$) | | | |
| A20 | <5/<5/1.4* | <5/<1.65/ <1.65/ 1.1 | <5/<10/<10 |
| MethA | n.t. | n.t. | n.t. |
| Toxicity | | | |
| MRC-5 | <6.67/<6.67 | 4 | 10 |
| RBC ($EC_{50}$) | 47 | 12* | n.t. |
| Anti-Cancer Selectivity | | | |
| MRC-5/A20 | (<4.8) | 3.6 | (>2) |
| RBC/A20 | 33.6 | 10.9 | n.t. |

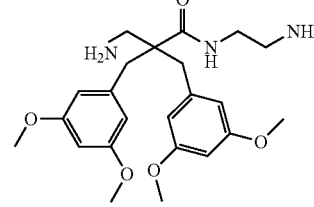

13

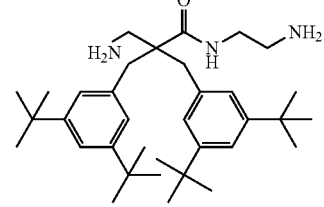

14

| | | |
|---|---|---|
| IUPAC-name | 3-amino-N-(2-aminoethyl)-2,2-bis(3,5-dimethoxy-benzyl)propanamide<br>Log P: 1.57<br>tPSA: 118.06<br>CLogP: 2.126 | 3-amino-N-(2-aminoethyl)-2,2-bis(3,5-di-tert-butylbenzyl)propanamide<br>Log P: 8.89<br>tPSA: 81.14<br>ClogP: 9.414 |
| Formula<br>Mw | $C_{23}H_{33}N_3O_5$<br>Exact Mass: 431.2420<br>Molecular Weight: 431.5252 | $C_{35}H_{57}N_3O$<br>Exact Mass: 535.4502<br>Molecular Weight: 535.8466 |
| Antimicrobial potency (MIC) | | |
| S. aureus | 200 | 3.75/5 |
| MRSA | 200 | 2.5 |
| MRSE | 100 | 2.5/5 |
| E. coli | >200 | 5/>20 |
| Anticancer potency ($IC_{50}$) | | |
| A20 | n.t. | n.t. |
| MethA | n.t. | n.t. |
| Toxicity | | |
| MRC-5 | 62.5/68 | 7.5/8.5 |
| RBC ($EC_{50}$) | >1000 | >62.5 [2*] |
| Anti-Cancer Selectivity | | |
| MRC-5/A20 | n.t. | n.t. |
| RBC/A20 | n.t. | n.t. |

*Low solubility in the test media.
n.t. = not tested
[2*] Highest concentration tested due to reduced water solubility.

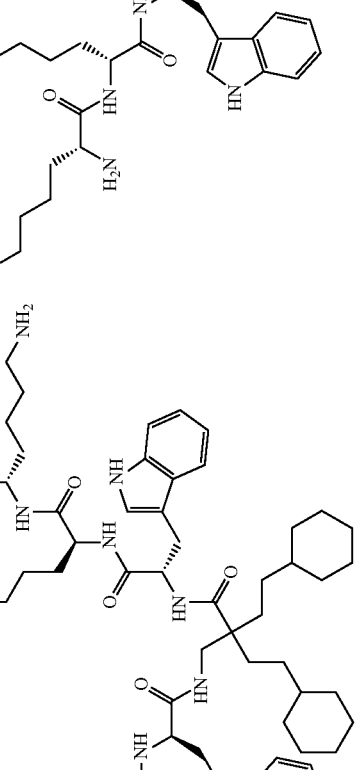

TABLE 3

Biological potency of hepta-β-peptides. (All values in μg/ml).

| | 15 | 16 |
|---|---|---|
| IUPAC-name | (R)-N-((2R,9S,12S,15S)-9-((1H-indol-3-yl)methyl)-19-amino-12-(4-aminobutyl)-15-carbamoyl-6,6-bis(2-cyclohexylethyl)-1-(1H-indol-3-yl)-2,6-diaminohexanamido)hexanamide | (R)-N-((2R,9S,12S,15S)-9-((1H-indol-3-yl)methyl)-19-amino-12-(4-aminobutyl)-6,6-dibenzyl-15-carbamoyl-1-(1H-indol-3-yl)-3,7,10,13-tetraoxo-4,8,11,14-tetraazanonadecan-2-yl)-6-amino-2-((R)-2,6-diaminohexanamido)hexanamide |
| Formula | $C_{65}H_{104}N_{14}O_7$ | $C_{63}H_{88}N_{14}O_7$ |
| Mw | Exact Mass: 1192.8212 Molecular Weight: 1193.6109 | Exact Mass: 1152.6960 Molecular Weight: 1153.4624 |
| Antimicrobial potency (MIC) | | |
| S. aureus | n.t. | n.t. |
| MRSA | n.t. | n.t. |
| MRSE | n.t. | n.t. |
| E. coli | n.t. | n.t. |
| Anticancer potency (IC$_{50}$) | | |
| A20 | 15.0 | 263 |
| MethA | n.t. | n.t. |
| Toxicity | | |
| MRC-5 | 45.7 | >500 |
| RBC (EC$_{50}$) | n.t. | n.t. |
| Anti-Cancer Selectivity | | |

TABLE 3-continued

Biological potency of hepta-β-peptides. (All values in µg/ml).

| | 17 | 18 |
|---|---|---|
| | 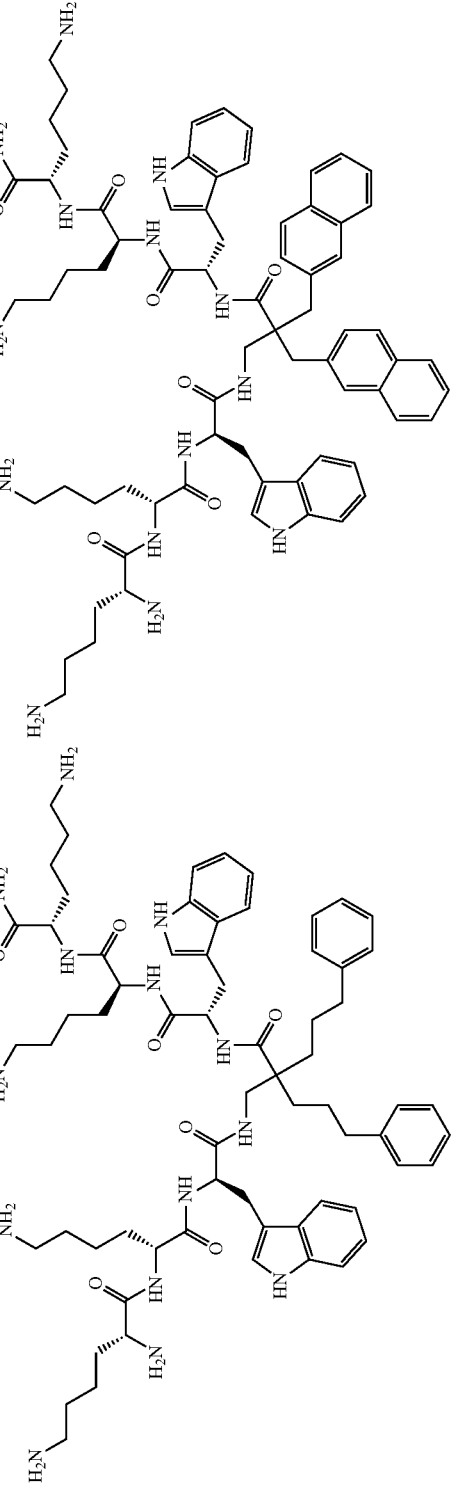 | 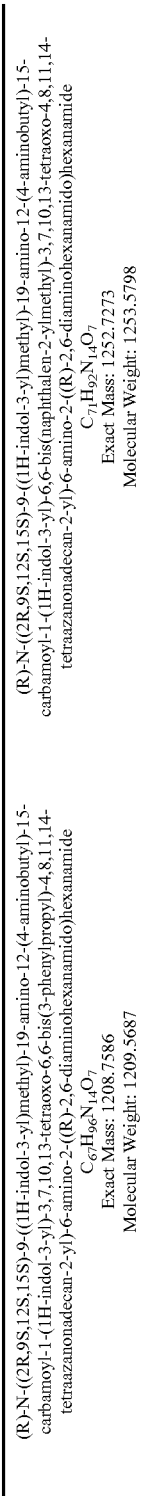 |
| IUPAC-name | (R)-N-((2R,9S,12S,15S)-9-((1H-indol-3-yl)methyl)-19-amino-12-(4-aminobutyl)-15-carbamoyl-1-(1H-indol-3-yl)-3,7,10,13-tetraoxo-6,6-bis(3-phenylpropyl)-4,8,11,14-tetraazanonadecan-2-yl)-6-amino-2-((R)-2,6-diaminohexanamido)hexanamide | (R)-N-((2R,9S,12S,15S)-9-((1H-indol-3-yl)methyl)-19-amino-12-(4-aminobutyl)-15-carbamoyl-1-(1H-indol-3-yl)-6,6-bis(naphthalen-2-ylmethyl)-3,7,10,13-tetraoxo-4,8,11,14-tetraazanonadecan-2-yl)-6-amino-2-((R)-2,6-diaminohexanamido)hexanamide |
| Formula | $C_{67}H_{96}N_{14}O_7$ | $C_{71}H_{92}N_{14}O_7$ |
| Mw | Exact Mass: 1208.7586<br>Molecular Weight: 1209.5687 | Exact Mass: 1252.7273<br>Molecular Weight: 1253.5798 |
| Antimicrobial potency (MIC) | | |
| S. aureus | n.t. | n.t. |
| MRSA | n.t. | n.t. |
| MRSE | n.t. | n.t. |
| E. coli | n.t. | n.t. |
| Anticancer potency (IC$_{50}$) | | |
| A20 | 26.5/40 * | 24 |
| MethA | n.t. | n.t. |
| Toxicity | | |
| MRC-5/A20 | 3.0 | (>1.9) |
| RBC/A20 | n.t. | n.t. |

TABLE 3-continued

Biological potency of hepta-β-peptides. (All values in μg/ml).

| | 19 | 20 |
|---|---|---|
| IUPAC-name | (R)-N-((2R,9S,12S,15S)-9-((1H-indol-3-yl)methyl)-19-amino-12-(4-aminobutyl)-15-carbamoyl-6,6-bis(4-fluorobenzyl)-1-(1H-indol-3-yl)-3,7,10,13-tetraoxo-4,8,11,14-tetraazanonadecan-2-yl)-6-amino-2-(R)-2,6-diaminohexanamido)hexanamide | (R)-N-((2R,9S,12S,15S)-9-((1H-indol-3-yl)methyl)-19-amino-12-(4-aminobutyl)-15-carbamoyl-6,6-bis(4-(trifluoromethyl)benzyl)-1-(1H-indol-3-yl)-3,7,10,13- tetraoxo-6,6-bis(4-(trifluoromethyl)benzyl)-4,8,11,14-tetraazanonadecan-2-yl)-6-amino-2-(R)-2,6-diaminohexanamido)hexanamide |
| Formula | $C_{63}H_{86}F_2N_{14}O_7$ | $C_{65}H_{86}F_6N_{14}O_7$ |
| Mw | Exact Mass: 1188.6772<br>Molecular Weight: 1189.4433 | Exact Mass: 1288.6708<br>Molecular Weight: 1289.4584 |
| Antimicrobial potency (MIC) | | |
| *S. aureus* | n.t. | n.t. |
| MRSA | n.t. | n.t. |
| MRSE | n.t. | n.t. |
| *E. coli* | n.t. | n.t. |
| Anticancer potency (IC$_{50}$) | | |
| A20 | 197 | 37 |
| MRC-5 | 241/221 * | 103 |
| RBC (EC$_{50}$) | n.t. | n.t. |
| Anti-Cancer Selectivity | | |
| MRC-5/A20 | 9.1/5.5 * | 4.3 |
| RBC/A20 | n.t. | n.t. |

TABLE 3-continued

Biological potency of hepta-β-peptides. (All values in μg/ml).

| | 21 | 22 |
|---|---|---|
| MethA Toxicity | n.t. | n.t. |
| MRC-5 RBC (EC$_{50}$) Anti-Cancer Selectivity | >500 n.t. | 260 n.t. |
| MRC-5/A20 RBC/A20 | (>2.5) n.t. | 7.0 n.t. |
| IUPAC-Name | (R)-N-((2R,9S,12S,15S)-9-((1H-indol-3-yl)methyl)-19-amino-12-(4-aminobutyl)-6,6-bis(4-tert-butylbenzyl)-15-carbamoyl-1-(1H-indol-3-yl)-3,7,10,13-tetraoxo-4,8,11,14-tetraazanonadecan-2-yl)-6-amino-2-((R)-2,6-diaminohexanamido)hexanamide | (R)-N-((2R,9S,12S,15S)-9-((1H-indol-3-yl)methyl)-19-amino-12-(4-aminobutyl)-15-carbamoyl-6,6-bis(3,5-dimethylbenzyl)-1-(1H-indol-3-yl)-3,7,10,13-tetraoxo-4,8,11,14-tetraazanonadecan-2-yl)-6-amino-2-((R)-2,6-diaminohexanamido)hexanamide |
| Formula Mw | C$_{71}$H$_{104}$N$_{14}$O$_{7}$<br>Exact Mass: 1264.8212<br>Molecular Weight: 1265.6751 | C$_{67}$H$_{96}$N$_{14}$O$_{7}$<br>Exact Mass: 1208.7586<br>Molecular Weight: 1209.5687 |
| Antimicrobial potency (MIC) | | |
| S. aureus MRSA MRSE | n.t. n.t. n.t. | n.t. n.t. n.t. |

TABLE 3-continued

Biological potency of hepta-β-peptides. (All values in µg/ml).

| | E. coli Anticancer potency (IC$_{50}$) | |
|---|---|---|
| A20 MethA Toxicity | 14.5/17.5 * n.t. | 32/40 * n.t. |
| MRC-5 RBC (EC$_{50}$) Anti-Cancer Selectivity | 42/55.2 * n.t. | 237/205 * n.t. |
| MRC-5/A20 RBC/A20 | 2.9/3.2 * n.t. | 7.4/5.1 * n.t. |

* The two sets of results are due to two individual screenings (and an average of three parallels in each screening)
n.t. = not tested

TABLE 4

Biological potency of β2,2-amino acid dimethylamino-ethyl derivatives. (All values in μg/ml).

| | 23 | 24 | 25 |
|---|---|---|---|
| IUPAC-Name | 3-amino-2,2-dibenzyl-N-(2-(dimethylamino)-ethyl)-propanamide<br>Log P: 2.97<br>tPSA: 58.36<br>CLogP: 3.0078 | 3-amino-2,2-bis(4-tert-butylbenzyl)-N-(2-(dimethylamino)-ethyl)-propanamide<br>Log P: 6.38<br>tPSA: 58.36<br>CLogP: 6.6598 | 3-amino-N-(2-(dimethylamino)-ethyl)-2,2-bis(3,5-dimethylbenzyl)-propanamide<br>Log P: 4.92<br>tPSA: 58.36<br>CLogP: 5.0038 |
| Formula<br>Mw | $C_{21}H_{29}N_3O$<br>Exact Mass: 339.2311<br>Molecular Weight: 339.4745 | $C_{29}H_{45}N_3O$<br>Exact Mass: 451.3563<br>Molecular Weight: 451.6871 | $C_{25}H_{37}N_3O$<br>Exact Mass: 395.2937<br>Molecular Weight: 395.5808 |
| Antimicrobial potency (MIC) | | | |
| S. aureus | >100 | 5 | 100 |
| MRSA | >100 | 5 | 50 |
| MRSE | >100 | 2.5 | 10 |
| E. coli | >100 | 5 | 50 |
| Anticancer potency ($IC_{50}$) | | | |
| A20 | n.t. | n.t. | n.t. |
| MethA | n.t. | n.t. | n.t. |
| Toxicity | | | |
| MRC-5 | n.t. | n.t. | n.t. |
| RBC ($EC_{50}$) | >1000 | 185 | 820 |
| Anti-Cancer Selectivity | | | |
| MRC-5/A20 | n.t. | n.t. | n.t. |
| RBC/A20 | n.t. | n.t. | n.t. |

| | 26 | 27 | 28 |
|---|---|---|---|
| IUPAC-Name | 2-(aminomethyl)-N-(2-(dimethyl-amino)ethyl)-5-phenyl-2-(3-phenyl-propyl)-pentanamide<br>Log P: 4.64<br>tPSA: 58.36<br>CLogP: 4.9738 | 3-amino-N-(2-(dimethylamino)ethyl)-2,2-bis(naphthalen-2-ylmethyl)propanamide<br>Log P: 4.97<br>tPSA: 58.36<br>CLogP: 5.3558 | 3-amino-N-(2-(dimethylamino)ethyl)-2,2-bis(4-(trifluoromethyl)benzyl)-propanamide<br>Log P: 4.82<br>tPSA: 58.36<br>CLogP: 4.7738 |
| Formula<br>Mw | $C_{25}H_{37}N_3O$<br>Exact Mass: 395.2937<br>Molecular Weight: 395.5808 | $C_{29}H_{33}N_3O$<br>Exact Mass: 439.2624<br>Molecular Weight: 439.5918 | $C_{23}H_{27}F_6N_3O$<br>Exact Mass: 475.2058<br>Molecular Weight: 475.4704 |
| Antimicrobial potency (MIC) | | | |
| S. aureus | 35 | 5 | 10 |
| MRSA | 35 | 5 | 5 |
| MRSE | 35 | 5 | 15 |

TABLE 4-continued

Biological potency of β2,2-amino acid dimethylamino-ethyl derivatives. (All values in μg/ml).

| | | | |
|---|---|---|---|
| *E. coli* | 100 | 15 | 35 |
| Anticancer potency (IC$_{50}$) | | | |
| A20 | n.t. | n.t. | n.t. |
| MethA | n.t. | n.t. | n.t. |
| Toxicity | | | |
| MRC-5 | n.t. | n.t. | n.t. |
| RBC (EC$_{50}$) | 316 | 145 | 329 |
| Anti-Cancer Selectivity | | | |
| MRC-5/A20 | n.t. | n.t. | n.t. |
| RBC/A20 | n.t. | n.t. | n.t. | n.t.-not tested

TABLE 5

Biological potency of β2,2-amino acid N-methyl piperazine derivatives. (All values in μg/ml).

| | 29 | 30 | 31 |
|---|---|---|---|
| IUPAC-Name | 3-amino-2,2-bis(4-tert-butylbenzyl)-1-(4-methylpiperazin-1-yl)propan-1-one | 3-amino-2,2-bis(3,5-dimethylbenzyl)-1-(4-methylpiperazin-1-yl)propan-1-one | 2-(aminomethyl)-1-(4-methylpiperazin-1-yl)-5-phenyl-2-(3-phenylpropyl)pentan-1-one |
| | Log P: 6.37 | Log P: 4.91 | Log P: 4.63 |
| | tPSA: 49.57 | tPSA: 49.57 | tPSA: 49.57 |
| | CLogP: 7.0724 | CLogP: 5.4164 | CLogP: 5.3864 |
| Formula | C$_{30}$H$_{45}$N$_3$O | C$_{26}$H$_{37}$N$_3$O | C$_{26}$H$_{37}$N$_3$O |
| Mw | Exact Mass: 463.36 | Exact Mass: 407.29 | Exact Mass: 407.29 |
| | Molecular Weight: 463.70 | Molecular Weight: 407.59 | Molecular Weight: 407.59 |
| Antimicrobial potency (MIC) | | | |
| *S. aureus* | 10 | >200 | 200 |
| MRSA | 10 | 200 | 200 |
| MRSE | 5 | 35 | 200 |
| *E. coli* | 10 | 200 | 200 |
| Anticancer potency (IC$_{50}$) | | | |
| A20 | n.t. | n.t. | n.t. |
| MethA | n.t. | n.t. | n.t. |
| Toxicity | | | |
| MRC-5 | n.t. | n.t. | n.t. |
| RBC (EC$_{50}$) | 241 | >1000 | >1000 |
| Anti-Cancer Selectivity | | | |
| MRC-5/A20 | n.t. | n.t. | n.t. |
| RBC/A20 | n.t. | n.t. | n.t. |

TABLE 5-continued

Biological potency of β2,2-amino acid N-methyl piperazine derivatives. (All values in μg/ml).

|  | 32 | 33 |
|---|---|---|
| IUPAC-Name | 3-amino-1-(4-methylpiperazin-1-yl)-2,2-bis(naphthalen-2-ylmethyl)propan-1-one<br>Log P: 4.96<br>tPSA: 49.57<br>CLogP: 5.7684 | 3-amino-1-(4-methylpiperazin-1-yl)-2,2-bis(4-(trifluoromethyl)benzyl)propan-1-one<br>Log P: 4.81<br>tPSA: 49.57<br>CLogP: 5.1864 |
| Formula Mw | $C_{30}H_{33}N_3O$<br>Exact Mass: 451.26<br>Molecular Weight: 451.60 | $C_{24}H_{27}F_6N_3O$<br>Exact Mass: 487.21<br>Molecular Weight: 487.48 |
| Antimicrobial potency (MIC) | | |
| S. aureus | 10 | 35 |
| MRSA | 5 | 10 |
| MRSE | 10 | 50 |
| E. coli | 15 | 50 |
| Anticancer potency (IC$_{50}$) | | |
| A20 | n.t. | n.t. |
| MethA | n.t. | n.t. |
| Toxicity | | |
| MRC-5 | n.t. | n.t. |
| RBC (EC$_{50}$) | 225 | 376 |
| Anti-Cancer Selectivity | | |
| MRC-5/A20 | n.t. | n.t. |
| RBC/A20 | n.t. | n.t. | n.t. = not tested

TABLE 6

Biological potency of β2,2-amino acid N,N-dimethylamino-ethyl-piperazin derivatives. (All values in μg/ml).

|  | 34 | 35 | 36 |
|---|---|---|---|
| IUPAC-Name | 3-amino-2,2-bis(4-tert-butylbenzyl)-1-(4-(2-(dimethylamino)ethyl)piperazin-1-yl)propan-1-one<br>Log P: 6.37<br>tPSA: 52.81<br>CLogP: 7.4475 | 3-amino-1-(4-(2-(dimethylamino)ethyl)piperazin-1-yl)-2,2-bis(3,5-dimethylbenzyl)propan-1-one<br>Log P: 4.91<br>tPSA: 52.81<br>CLogP: 5.7915 | 2-(aminomethyl)-1-(4-(2-(dimethylamino)ethyl)piperazin-1-yl)-5-phenyl-2-(3-phenylpropyl)pentan-1-one<br>Log P: 4.63<br>tPSA: 52.81<br>CLogP: 5.7615 |
| Formula Mw | $C_{33}H_{52}N_4O$<br>Exact Mass: 520.41<br>Molecular Weight: 520.79 | $C_{29}H_{44}N_4O$<br>Exact Mass: 464.35<br>Molecular Weight: 464.69 | $C_{29}H_{44}N_4O$<br>Exact Mass: 464.35<br>Molecular Weight: 464.69 |
| Antimicrobial potency (MIC) | | | |
| S. aureus | 10 | 50 | 200 |
| MRSA | 10 | 50 | 50 |
| MRSE | 10 | 35 | 50 |

TABLE 6-continued

Biological potency of β2,2-amino acid N,N-dimethylamino-ethyl-piperazin derivatives. (All values in μg/ml).

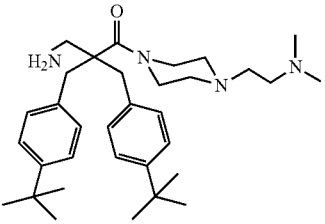 [SMILES: CN(C)CCN1CCN(C(=O)C(CN)(Cc2ccc(C(C)(C)C)cc2)Cc2ccc(C(C)(C)C)cc2)CC1]

| | 34 | 35 | 36 |
|---|---|---|---|
| *E. coli* | 10 | 100 | 200 |
| Anticancer potency ($IC_{50}$) | | | |
| A20 | n.t. | n.t. | n.t. |
| MethA | n.t. | n.t. | n.t. |
| Toxicity | | | |
| MRC-5 | n.t. | n.t. | n.t. |
| RBC ($EC_{50}$) | 252 | n.t. | >1000 |
| Anti-Cancer Selectivity | | | |
| MRC-5/A20 | n.t. | n.t. | n.t. |
| RBC/A20 | n.t. | n.t. | n.t. | n.t. = not tested

TABLE 7

(All values in μg/ml).

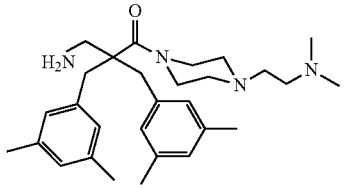

| | 37 | 38 |
|---|---|---|
| IUPAC-Name | 3-amino-1-(4-(2-(dimethylamino)ethyl)piperazin-1-yl)-2,2-bis(naphthalen-2-ylmethyl)propan-1-one | 3-amino-1-(4-(2-(dimethylamino)ethyl)piperazin-1-yl)-2,2-bis(4-(trifluoromethyl)benzyl)propan-1-one |
| | Log P: 4.96 | Log P: 4.81 |
| | tPSA: 52.81 | tPSA: 52.81 |
| | CLog P: 6.1435 | CLogP: 5.5615 |
| Formula | $C_{33}H_{40}N_4O$ | $C_{27}H_{34}F_6N_4O$ |
| Mw | Exact Mass: 508.3202 | Exact Mass: 544.2637 |
| | Molecular Weight: 508.6969 | Molecular Weight: 544.5755 |
| Antimicrobial potency (MIC) | | |
| *S. aureus* | 15 | 35 |
| MRSA | 2.5 | 5 |
| MRSE | 10 | 50 |
| *E. coli* | 35 | 100 |
| Anticancer potency ($IC_{50}$) | | |
| A20 | n.t. | n.t. |
| MethA | n.t. | n.t. |

TABLE 7-continued (All values in µg/ml).

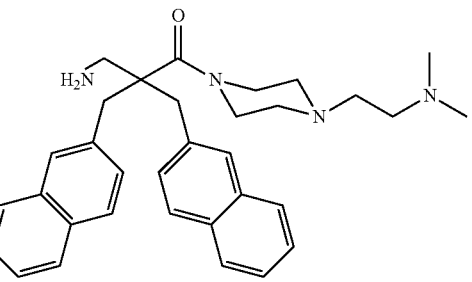

| | 37 | 38 |
|---|---|---|
| Toxicity | | |
| MRC-5 | n.t. | n.t. |
| RBC (EC$_{50}$) | 301 | 862 |
| Anti-Cancer Selectivity | | |
| MRC-5/A20 | n.t. | n.t. |
| RBC/A20 | n.t. | n.t. | n.t. = not tested

Example 3

Compound 7 described in Example 2 was screened against two normal cell lines and nine cancer cell lines.

All cell lines were of human origin. Stock solution of compound 7 was dissolved in assay media containing 10% DMSO. Three parallel experiments were performed against each cell line.

Previous results for compound 7 against A20 cancer cells gave IC$_{50}$ 0.7 µg/ml, and against RBC EC$_{50}$ 292 µg/ml (Table 2). Previous tests of compound 7 against MRC-5 cells gave IC$_{50}$ 13.5 and 14 µg/ml whereas the panel screening gave IC$_{50}$ 8.21 µg/ml.

TABLE 8

Results from the compound 7 panel screening against two normal cell lines (MRC-5 and HUV-EC-C) and nine cancer cell lines.

| Cell line | Organ | Disease | Cell type | THAP164 IC50 µg/ml |
|---|---|---|---|---|
| MRC-5s | Lung | Normal | Fibroblast | 8.21 |
| HUV-EC-C | Umbilical vein | Normal | Endothelial | 3.81 |
| DU-145 | Prostate | Carcinoma | Epithelial | 15.21 |
| OVCAR-3 | Ovary | Adenocarcinoma | Epithelial | 18.05 |
| MDA-MB435 | Breast | Carcinoma | N/A | 6.54 |
| FEMX | Skin | Melanoma | N/A | 17.1 |
| UT-SCC-24A | Tongue | Squamous oral carcinoma | Primary Oral Cancer cell | 14.19 |
| UT-SCC-34A | Supraglottic larynx | Squamous oral carcinoma | Primary Oral Cancer cell | 16.18 |
| HT-29 | Colon | Colorectal adenocarcinoma | Epithelial | 15.45 |
| Ramos | N/A | Burkitt's lymphoma | B lymphocyte | 2.61 |
| Kelly | N/A | Neuroblastoma | N/A | 3.90 |

Example 4

$\beta^{2,2}$-amino acid derivatives of the invention were made and tested for antimicrobial activity and investigated for their suitability for oral administration.

Synthesis

Figure 3:
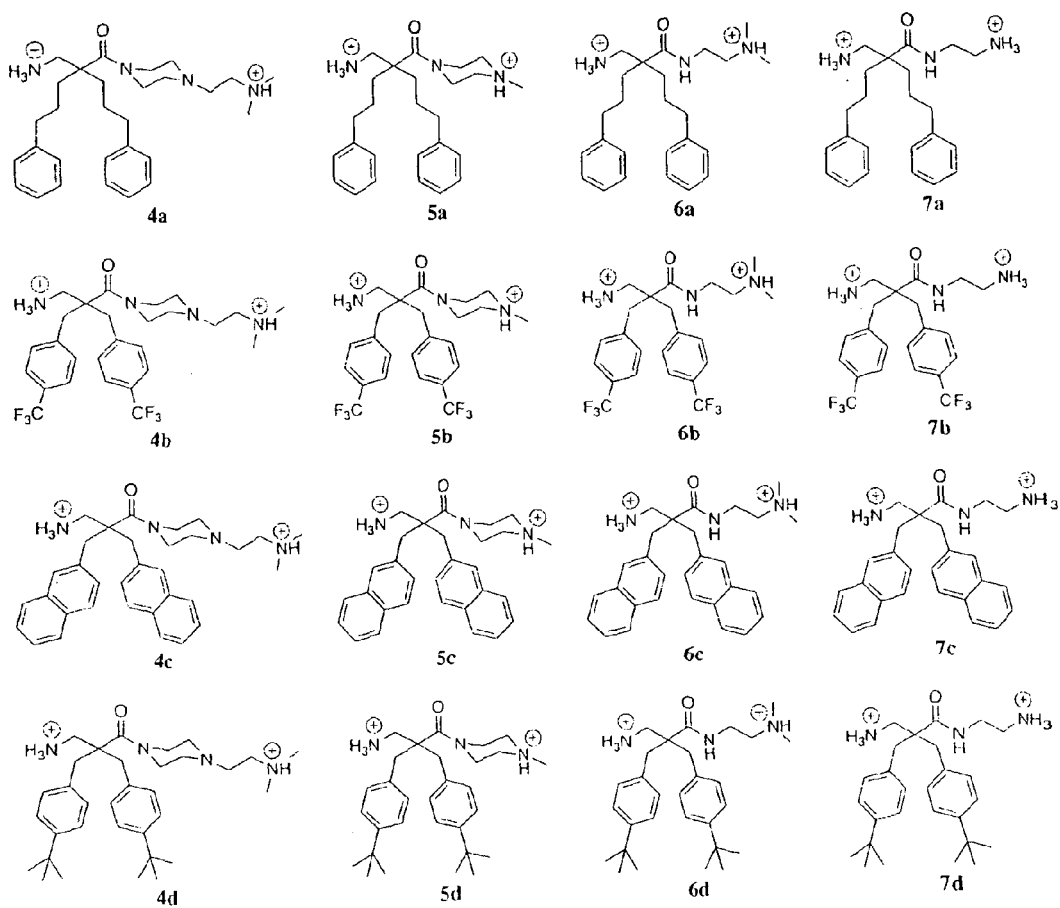
FIG. 3 shows compounds 4a-d, 5a-d, 6a-d and 7a-d of Example 4.

The $\beta^{2,2}$-amino acid derivatives (FIG. 3) were synthesized according to the strategies shown in FIG. 4. For a review covering a wide range of methods for preparing β-amino see Abele, S. et al. Eur. J. Org. Chem. [2000] 2000, 1-15. The Boc-protected $\beta^{2,2}$-amino acids 3a-d were coupled to four different C-terminal cationic groups (FIG. 4). In order to improve the yields, 1.5 eq. of the coupling reagent TFFH was used in the final coupling step, and the $\beta^{2,2}$-amino acids were also pre-activated for 2 h with TFFH instead of the standard 10 min. The coupling reactions were followed by mass spectrometric analysis and terminated by addition of aqueous Na$_2$CO$_3$. However, due to sterical hindrance the coupling time had to be extended up to 7 days for attachment of the C-terminal cationic groups.

General Procedure for Synthesis of 1a-d.

The synthesis was based on a previous reported synthesis by Cronin et al. Anal. Biochem. [1982] 124, 139-149. In brief, sodium methoxide (20 mmol) was dissolved in methanol to achieve an approximate concentration of 0.2 M before methyl cyanoacetate (20 mmol) was added and the reaction mixture was stirred for 5 min at r.t. The desired benzyl bromide (20 mmol) was added and the solution was heated to refluxed for 15 min before the solution was cooled to r.t. and a second portion of sodium methoxide (20 mmol) was added. After 5 min stirring at r.t. another portion of the desired benzyl bromide (20 mmol) was added, followed by another 15 min reflux. Approximately ⅔ of the methanol was removed in vacuo before the reaction mixture was diluted with ethyl acetate and washed with water. The organic phase was dried over MgSO$_4$, filtered and evaporated to dryness. The product 1a-d was used in following Synthesis without any further purification.

General Procedure for Synthesis of 2a-d.

The synthesis was based on previous reported synthesis by Cronin et al. supra and Bodanszky et al. "The practice of peptide synthesis" Springe-Verlag 1994. In brief, Ra/Ni (typically 2 mL) was washed with methanol to remove water before the desired methyl cyanoacetate derivative (1a-d) (3.5 mmol) was added along with acetic acid (typically 1 ml) and methanol to yield a final concentration of 1a-d of approximately 0.1 M. The reaction mixture was hydrogenated at 45° C. with a reflux condenser mounted for 5 days with 1 bar $H_2$ before the Ra/Ni was filtered off and the reaction mixture was evaporated to dryness. The crude $\beta^{2,2}$-amino acid methyl ester was dissolved in a mixture of 1,4-dioxane and water 5:1 (0.35 M) and the pH adjusted to 8 with TEA before $Boc_2O$ (1.5 eq) dissolved in as little as possible 1,4-dioxane was added and the solution was stirred at r.t. for 18 h. The reaction mixture was acidified to pH 4-5 with 0.1 M HCl and extracted three times with ethyl acetate before the organic phase was dried over $MgSO_4$, filtered, and evaporated to dryness. The crude product 2a-d was used in the following synthesis without any further purification.

General Procedure for Synthesis of 3a-d.

The synthesis was based on a publication by Seebach et al. Hely. Chim. Acta [1998] 81, 2218-2243. In brief, the crude Boc-protected $\beta^{2,2}$-amino acid methyl ester 2a-d (0.35 mmol) was dissolved in a mixture of 1,4-dioxane and water 3:1 to achieve a final concentration of approximately 1.2 mM before lithium hydroxide (2.1 mmol) dissolved in as little water as possible was added. The reaction mixture was heated to reflux and left for 18 h before the volume was reduced to approximately ⅕ in vacuo and the pH was adjusted to 1-2 by slowly addition of 0.1 M HCl. The aqueous solution was extracted three times with ethyl acetate before the organic phase was dried over $MgSO_4$, filtered, and evaporated to dryness. The crude product 3a-d was used in the following synthesis without any further purification.

General Procedure for Synthesis of 4a-d, 5a-d, 6a-d, and 7a-d.

The synthesis was based on the textbook of Chan and White, "Fmoc solid phase peptide synthesis: a practical approach", Oxford University Press 2000; p 346. In brief, the Boc-protected $\beta^{2,2}$-amino acid (3a-d) (typically 0.2 mmol) was dissolved in DMF (0.02 M) and DIPEA (3 eq.) was added along with TFFH (1 eq.). The $\beta^{2,2}$-amino acids was activated for 2 h before the desired amine was added (2 eq.). The reactions were followed by MS, and allowed to react for up to 7 days before it was diluted with ethyl acetate and washed with brine. The organic phase was dried over $MgSO_4$, filtered, and evaporated to dryness. The Boc-protected $\beta^{2,2}$-amino acid derivatives were deprotected by dissolving them in DCM, adding an equivalent volume of TFA:TIS:water (95: 2.5:2.5) and stirred at r.t. for 2 h before evaporated to dryness. The crude product was purified by preparative RPHPLC and lyophilized. The purity of the compounds was checked by analytical HPLC with PDA detector spanning from 210 nm to 310 nm. All compounds possessed purity above 95%.

Antimicrobial Activity

Each compound was tested in duplicates at 200, 100, 50, 35, 15, 10, 5, 2.5, 1, 0.5 µg/ml. All tested compounds were di-trifluoroacetic acid salts.

Hemolytic Activity

The plasma fraction of heparinized human blood was first removed by centrifugation and three additional washing steps with 37° C. pre-warmed phosphate buffered saline (PBS). Subsequently, the human RBC were diluted to 10% hematocrit and the $\beta^{2,2}$-amino acid derivatives were dissolved in PBS providing concentrations ranging from 1-1000 µg/mL. The diluted RBC were added to the compound solutions to a final erythrocyte concentration of 1% v/v. PBS and TRITON X-100 (non-ionic surfactant), in a final concentration of 0.1% v/v, were included as negative and positive control. After 1 hour agitated incubation at 37° C. the samples were centrifuged at 4000 rpm for 5 min. Release of hemoglobin was determined by measuring the absorbance of the supernatant at 405 nm. Hemolytic activity was calculated as the ratio of treated sample with $\beta^{2,2}$-amino acid derivative and tenside treated sample according to the formula:

$$[\%] \text{ Hemolysis} = \frac{\text{Abs}[\beta^{2,2} - \text{amino acid}] - \text{Abs}[\text{Negative control}]}{\text{Abs}[\text{Positive control}] - \text{Abs}[\text{Negative control}]} \times 100$$

TABLE 9

Minimal inhibitory concentration (MIC in µM) against MRSA, MRSE, S. aureus, E. coli, and P. aeruginosa, and hemolytic activity (EC50 in µM) against human RBC for a series of small $\beta^{2,2}$-amino acid derivatives. A therapeutic index was calculated by dividing the EC50 RBC values by the MIC values against each bacterial strain.

| | MIC[a] | | | | | $EC_{50}$[b] | Therapeutic index | | | | |
|---|---|---|---|---|---|---|---|---|---|---|---|
| Entry | MTRSA[c] | MRSE[d] | S. aureus[e] | E. coli[f] | P. aeruginosa[g] | RBC[h] | MRSA | MRSE | S. aureus | E. coli | P. aeruginosa |
| 4a | 72 | 72 | 289 | 289 | | — | | | | | |
| 4b | 6.5 | 65 | 45 | 129 | | 1116 | 172 | 17 | 25 | 8.6 | |
| 4c | 3.4 | 14 | 20 | 48 | | 409 | 120 | 29 | 20 | 8.5 | |
| 4d | 13 | 13 | 13 | 13 | 255 | 337 | 26 | 26 | 26 | 26 | 1.3 |
| 5a | 315 | 315 | 315 | 315 | | — | | | | | |
| 5b | 14 | 70 | 49 | 70 | | 525 | 38 | 7.5 | 11 | 7.5 | |
| 5c | 7.4 | 15 | 15 | 22 | — | 303 | 41 | 20 | 20 | 14 | |
| 5d | 15 | 7.2 | 15 | 15 | 289 | 348 | 23 | 48 | 23 | 23 | 1.2 |
| 6a | 56 | 56 | 56 | 160 | | 507 | 9.1 | 9.1 | 9.1 | 3.2 | |
| 6b | 7.1 | 21 | 14 | 50 | | 468 | 66 | 22 | 33 | 9.4 | |
| 6c | 7.5 | 7.5 | 7.5 | 23 | 300 | 117 | 16 | 16 | 16 | 5.1 | 0.4 |
| 6d | 7.4 | 3.7 | 7.4 | 7.4 | 74 | 274 | 37 | 74 | 37 | 37 | 3.7 |
| 7a | 59 | 25 | 71 | 336 | | 1377 | 23 | 55 | 19 | 4.1 | |
| 7b | 7.4 | 15 | 15 | 52 | | 425 | 57 | 28 | 28 | 8 | |

TABLE 9-continued

Minimal inhibitory concentration (MIC in μM) against MRSA, MRSE, S. aureus, E. coli, and P. aeruginosa, and hemolytic activity (EC50 in μM) against human RBC for a series of small $\beta^{2,2}$-amino acid derivatives. A therapeutic index was calculated by dividing the EC50 RBC values by the MIC values against each bacterial strain.

| | MIC[a] | | | | | EC$_{50}$[b] | Therapeutic index | | | | |
|---|---|---|---|---|---|---|---|---|---|---|---|
| Entry | MTRSA[c] | MRSE[d] | S. aureus[e] | E. coli[f] | P. aeruginosa[g] | RBC[h] | MRSA | MRSE | S. aureus | E. coli | P. aeruginosa |
| 7c | 7.8 | 3.9 | 3.9 | 24 | 55 | 457 | 59 | 117 | 117 | 19 | 8.3 |
| 7d | 3.8 | 3.8 | 3.8 | 7.7 | 23 | 18 | 4.7 | 4.7 | 4.7 | 2.3 | 0.8 |

Highest concentrations tested were [a]200 μg/ml and [b]1000 μg/ml.
All $\beta^{2,2}$-amino acid derivatives were isolated as their di-trifluoroacetate salts, and the molar concentrations were calculated as such.
[c]Methicillin resistant Staphylococcus aureus (ATCC 33591),
[d]Methicillin resistant Staphylococcus epidermidis (ATCC 27626),
[e]Staphylococcus aureus (ATCC 25923),
[f]Escherichia coli (ATCC 25922),
[g]Pseudomonas aeruginosa (ATCC 27853) and
[h]human red blood cells.
The notation "—" denotes no detectable activity (MIC or EC50) within the concentration range tested.

Drug-Likeness and Oral Absorption

By using the Schrödinger's QikProp application that is included in the Schrödinger's Maestro software v9.1, an evaluation of the drug-likeness of the $\beta^{2,2}$-amino acid derivatives with respect to the Lipinski's rule of five was assessed together with an estimation of percentage oral absorption in humans. The rules state that an oral active drug should not violate more than one of the following four criteria; 1) the octanol-water partition coefficient log P should be less than 5, 2) the molecular mass (Mw) should not exceed 500 daltons, 3) a maximum of 5 hydrogen bond donor (HBD) groups is tolerated, and 4) there should be no more than 10 hydrogen bond acceptor (HBA) groups. The results are presented in Table 10 below.

TABLE 10

Evaluation of drug-likeness of the prepared $\beta^{2,2}$-amino acid derivatives with respect to the Lipinski's rule of five and calculation of potential oral absorption in humans.

| | Lipinski's rule of five (highest permitted value) | | | | Calc. oral |
|---|---|---|---|---|---|
| Comp. | Mw [a](500) | HBD [b](5) | HBA [c](10) | Log P [d](5) | abs. [e](%) |
| 4a | 464.7 | 1 | 7 | 3.8 | 72 |
| 4b | 544.6 | 1 | 7 | 4.2 | 62 |
| 4c | 508.7 | 1 | 7 | 4.3 | 63 |
| 4d | 520.8 | 1 | 7 | 4.8 | 66 |
| 5a | 407.6 | 1 | 5 | 3.9 | 86 |
| 5b | 487.5 | 1 | 5 | 4.4 | 88 |
| 5c | 451.6 | 1 | 5 | 4.3 | 87 |
| 5d | 463.7 | 1 | 5 | 5.1 | 79 |
| 6a | 395.6 | 2 | 4.5 | 3.8 | 84 |
| 6b | 475.5 | 2 | 4.5 | 4.6 | 89 |
| 6c | 439.6 | 2 | 4.5 | 4.7 | 89 |
| 6d | 451.7 | 2 | 4.5 | 5.3 | 80 |
| 7a | 367.5 | 4 | 3.5 | 2.9 | 73 |
| 7b | 447.4 | 4 | 3.5 | 3.4 | 71 |
| 7c | 411.5 | 4 | 3.5 | 3.4 | 72 |
| 7d | 423.6 | 4 | 3.5 | 3.7 | 73 |

[a]Molecular weights were calculated for non-ionized $\beta^{2,2}$-amino acid derivatives.
[b]Calculated number of hydrogen bond donor (HBD) groups.
[c]Calculated number of hydrogen bond acceptor (HBA) groups. The values were averages over a number of configurations; hence the non-integer values.
[d]Calculated octanol-water partition coefficient log P.
[e]Calculated percent oral absorption in humans. All predictions were calculated using the Schrödinger QikProp application included in the Schrödinger's Maestro software v9.1.

The results from the calculations revealed that all the $\beta^{2,2}$-amino acid derivatives fulfilled the Lipinski's rule of five since none of the compounds violated more than one of the four rules. A single rule was violated by 5 of the 16 $\beta^{2,2}$-amino acid derivatives prepared, in which three of these violations were due to a molecular mass above 500 (4b, 4c, and 4d), while the other two were due to a log P value above the limit of 5 (5d and 6d).

Calculation of percentage oral absorption in humans by the software concluded that all the $\beta^{2,2}$-amino acid derivatives were likely to be absorbed rather well by having a calculated oral absorption in the range of 62% to 89%. Highest percentage oral absorption was calculated for the $\beta^{2,2}$-amino acid derivatives 5a, 5b, 5c, 6b, and 6c, which all were in the range of 86%-89% oral absorption.

Permeability

Encouraged by the theoretical calculations, the permeability of the $\beta^{2,2}$-amino acid derivatives was further investigated using a recently established phospholipid vesicle based barrier model (Flaten et al. Eur. J. Pharm. Sci. [2006] 27, 80-90). Four $\beta^{2,2}$-amino acid derivatives (4c, 5c, 6c and 7c), which showed similar potency against MRSA and against E. coli were investigated. Based on the model's classification of absorption, all four compounds showed permeability equivalent to being moderately absorbed in humans. For the experimental permeability values, compound 5c showed highest permeability followed by compounds 6c, 4c, and 7c.

The invention claimed is:

1. A method of treating a bacterial infection, which method comprises administering to a subject in need of such treatment a peptide, peptidomimetic or amino acid derivative having a net positive charge of at least +2 and incorporating a group of formula I:

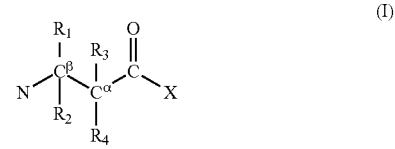

(I)

wherein any 2 from $R_1$, $R_2$, $R_3$ and $R_4$ are hydrogen atoms and 2 are substituting groups, which may be the same or different, comprise at least 7 non-hydrogen atoms, are lipophilic and include a cyclic group, said cyclic group not being attached directly either to the α or β carbon atom and optionally being linked or fused to a cyclic group in the other substituting group, where cyclic groups are fused the combined total number of non-hydrogen atoms for the two substituting groups is at least 12, and wherein X represents O, C, N or S, and wherein said peptide, peptidomimetic or amino acid derivative is 1 to 4 amino acids or equivalent subunits in length.

2. The method as claimed in claim 1 wherein the two substituting groups are the same.

3. The method as claimed in claim 1 wherein the group of formula I is a $\beta^{2,2}$ or $\beta^{3,3}$ distributed amino acid.

4. The method as claimed in claim 1 wherein each of the lipophilic substituting groups comprises an optionally substituted phenyl or cyclohexyl group.

5. The method as claimed in claim 4 wherein said phenyl or cyclohexyl groups are separated from the α or β carbon atom of the group of formula I by 1 to 4 linking atoms.

6. The method as claimed in claim 1 wherein each of the lipophilic substituting groups comprises 8 to 12 non-hydrogen atoms.

7. The method as claimed in claim 1 wherein the C terminus of the peptide, peptidomimetic or amino acid derivative is amidated and optionally substituted.

8. The method as claimed in claim 1 wherein the peptide or peptidomimetic incorporates a cationic amino acid.

9. The method as claimed in claim 8 wherein the cationic amino acid is arginine or lysine.

10. A method of treating tumour cells comprising administering to a subject in need of such treatment a peptide, peptidomimetic or amino acid derivative having a net positive charge of at least +2 and incorporating a group of formula I:

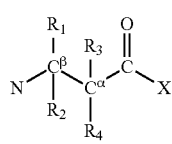

wherein any 2 from $R_1$, $R_2$, $R_3$ and $R_4$ are hydrogen atoms and 2 are substituting groups, which may be the same or different, comprise at least 7 non-hydrogen atoms, are lipophilic and include a cyclic group, said cyclic group not being attached directly either to the α or β carbon atom and optionally being linked or fused to a cyclic group in the other substituting group, where cyclic groups are fused the combined total number of non-hydrogen atoms for the two substituting groups is at least 12, and wherein X represents O, C, N or S, and wherein said peptide, peptidomimetic or amino acid derivative is 1 to 4 amino acids or equivalent subunits in length, wherein the tumour cell is selected from the group consisting of prostate carcinoma, ovarian adenocarcinoma, breast carcinoma, melanoma, squamous oral carcinoma, and colorectal adenocarcinoma.

11. The method as claimed in claim 10 wherein the two substituting groups are the same.

12. The method as claimed in claim 10 wherein the group of formula I is a $\beta^{2,2}$ or $\beta^{3,3}$ disubstituted amino acid.

13. The method as claimed in claim 10 wherein each of the lipophilic substituting groups comprises an optionally substituted phenyl or cyclohexyl group.

14. The method as claimed in claim 13 wherein said phenyl or cyclohexyl groups are separated from the α or β carbon atom of the group of formula I by 1 to 4 linking atoms.

15. The method as claimed in claim 10 wherein each of the lipophilic substituting groups comprises 5 to 12 non-hydrogen atoms.

16. The method as claimed in claim 10 wherein the C terminus of the peptide, peptidomimetic or amino acid derivative is amidated and optionally substituted.

17. The method as claimed in claim 10 wherein the peptide or peptidomimetic incorporates a cationic amino acid.

18. The method as claimed in claim 17 wherein the cationic amino acid is arginine or lysine.

19. An ex vivo method of bacterial cell lysis comprising contacting said bacterial cells with a peptide, peptidomimetic or amino acid derivative having a net positive charge of at least +2 and incorporating a group of formula I:

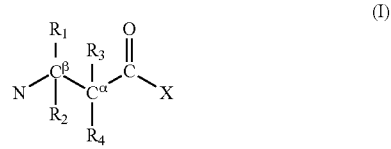

wherein any 2 from $R_1$, $R_2$, $R_3$ and $R_4$ are hydrogen atoms and 2 are substituting groups, which may be the same or different, comprise at least 7 non-hydrogen atoms, are lipophilic and include a cyclic group, said cyclic group not being attached directly either to the α or β carbon atom and optionally being linked or fused to a cyclic group in the other substituting group, where cyclic groups are fused the combined total number of non-hydrogen atoms for the two substituting groups is at least 12, and wherein X represents O, C, N or S, and wherein said peptide, peptidomimetic or amino acid derivative is 1 to 4 amino acids or equivalent subunits in length.

20. The method as claimed in claim 19 wherein the two substituting groups are the same.

21. The method as claimed in claim 19 wherein the group of formula I is a $\beta^{2,2}$ or $\beta^{3,3}$ disubstituted amino acid.

22. The method as claimed in claim 19 wherein each of the lipophilic substituting groups comprises an optionally substituted phenyl or cyclohexyl group.

23. The method as claimed in claim 19 wherein said phenyl or cyclohexyl groups are separated from the α or β carbon atom of the group of formula I by 1 to 4 linking atoms.

24. The method as claimed in claim 19 wherein each of the lipophilic substituting groups comprises 8 to 12 non-hydrogen atoms.

25. The method as claimed in claim 19 wherein the C terminus of the peptide, peptidomimetic or amino acid derivative is amidated and optionally substituted.

26. The method as claimed in claim 19 wherein the peptide or peptidomimetic incorporates a cationic amino acid.

27. The method as claimed in claim 26 wherein the cationic amino acid is arginine or lysine.

28. A peptide, peptidomimetic or amino acid derivative having a net positive charge of at least +2 which incorporates a group of formula I:

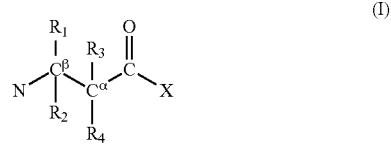

wherein any 2 from $R_1$, $R_2$, $R_3$ and $R_4$ are hydrogen atoms and 2 are substituting groups, which may be the same or different, comprise at least 7 non-hydrogen atoms, are lipophilic and include a cyclic group, said cyclic group not being attached directly either to the α or β carbon atom and optionally being linked or fused to a cyclic group in the other substituting group, where cyclic groups are fused the combined total number of non-hydrogen atoms for the two substituting groups is at least 12, and wherein X represents O, C, N or S, and wherein said peptide, peptidomimetic or amino acid derivative is 1 to 4 amino acids or equivalent subunits in length.

29. A formulation comprising the peptide, peptidomimetic or amino acid derivative as claimed in claim 28 and a diluent, carrier or excipient.

30. The peptide, peptidomimetic or amino acid derivative as claimed in claim 28 wherein the two substituting groups are the same.

31. The peptide, peptidomimetic or amino acid derivative as claimed in claim 28 wherein the group of formula I is a $\beta^{2,2}$ or $\beta^{3,3}$ disubstituted amino acid.

32. The peptide, peptidomimetic or amino acid derivative as claimed in claim 28 wherein each of the lipophilic substituting groups comprises an optionally substituted phenyl or cyclohexyl group.

33. The peptide, peptidomimetic or amino acid derivative as claimed in claim 32 wherein said phenyl of cyclohexyl groups are separated from the $\alpha$ or $\beta$ carbon atom of the group of formula I by 1 to 4 linking atoms.

34. The peptide, peptidomimetic or amino acid derivative as claimed in claim 28 wherein each of the lipophilic substituting groups comprises 8 to 12 non-hydrogen atoms.

35. The peptide, peptidomimetic or amino acid derivative as claimed in claim 28 wherein the C terminus of the peptide, peptidomimetic or amino acid derivative is amidated and optionally substituted.

36. The peptide, peptidomimetic or amino acid derivative as claimed in claim 28 wherein the peptide or peptidomimetic incorporates a cationic amino acid.

37. The peptide, peptidomimetic or amino acid derivative as claimed in claim 36 wherein the cationic amino acid is arginine or lysine.

* * * * *